United States Patent
Block et al.

(10) Patent No.: US 11,454,634 B2
(45) Date of Patent: Sep. 27, 2022

(54) ASSESSING WHETHER A SUBJECT SHALL BE SUBJECTED TO IMAGING BASED DIAGNOSTIC

(71) Applicant: Roche Diagnostics Operations, Inc., Indianapolis, IN (US)

(72) Inventors: Dirk Block, Bichl (DE); Roberto Latini, Milan (IT); Serge Masson, Monza (IT); Ursula-Henrike Wienhues-Thelen, Krailling (DE); Christian Zaugg, Rheinfelden (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/911,699

(22) Filed: Mar. 5, 2018

(65) Prior Publication Data
US 2018/0196067 A1    Jul. 12, 2018

Related U.S. Application Data

(63) Continuation of application No. 14/644,695, filed on Mar. 11, 2015, now abandoned, which is a continuation of application No. PCT/EP2013/056706, filed on Mar. 28, 2013.

(30) Foreign Application Priority Data

Sep. 12, 2012   (EP) ..................... 12184085

(51) Int. Cl.
*G01N 33/68*    (2006.01)
*A61B 5/055*    (2006.01)
*A61B 8/08*    (2006.01)

(52) U.S. Cl.
CPC .......... *G01N 33/6887* (2013.01); *A61B 5/055* (2013.01); *A61B 8/0883* (2013.01); *G01N 2333/4703* (2013.01); *G01N 2333/4706* (2013.01); *G01N 2333/4712* (2013.01); *G01N 2333/50* (2013.01); *G01N 2333/78* (2013.01); *G01N 2800/32* (2013.01); *G01N 2800/329* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 6,709,855 B1 | 3/2004 | Stanton et al. | |
| 2003/0109420 A1* | 6/2003 | Valkirs | G01N 33/6887 435/7.1 |
| 2004/0121343 A1* | 6/2004 | Buechler | C12Q 1/6883 435/6.14 |
| 2005/0095646 A1* | 5/2005 | Sherman | G01N 33/54306 435/7.1 |
| 2006/0286680 A1* | 12/2006 | Kang | G01N 33/54373 436/518 |
| 2008/0027330 A1* | 1/2008 | Naghavi | A61B 5/0402 600/481 |
| 2010/0021903 A1* | 1/2010 | Johnson | C12Q 1/6883 435/6.11 |
| 2011/0183434 A1* | 7/2011 | Wolf | G01N 33/74 436/501 |
| 2011/0237513 A1* | 9/2011 | Kas | A61P 13/08 514/15.4 |
| 2012/0142632 A1 | 6/2012 | Campbell | |

FOREIGN PATENT DOCUMENTS

| | | |
|---|---|---|
| JP | 2005-291899 A | 10/2005 |
| WO | 2008/089994 A1 | 7/2008 |
| WO | 2008/134054 A1 | 11/2008 |
| WO | 2008/144034 A1 | 11/2008 |
| WO | 2009/091556 A2 | 7/2009 |
| WO | 2010/054016 A1 | 5/2010 |
| WO | 2010/124821 A1 | 11/2010 |
| WO | 2011/075744 A1 | 6/2011 |
| WO | 2012/025355 A1 | 3/2012 |
| WO | 2012/029837 A1 | 3/2012 |

OTHER PUBLICATIONS

Smith et al., Am J Kidney Dis., 61(1), (2013), p. 67-73 (published online Aug. 9, 2012) (Year: 2012).*
Ford et al., Nephrol. Dial. Transplant, 27, (2012), p. 727-733 (Year: 2012).*
Löwbeer et al., Serum cardiac troponin T in patients hospitalized with heart failure is associated with left ventricular hypertrophy and systolic dysfunction, Scandinavian Journal of Clinical Laboratory Investigation, 64(7), (2004), p. 667-676 (Year: 2004).*
Franz et al., Time Course of Complete Normalization of Left Ventricular Hypertrophy During Long-Term Antihypertensive Therapy With Angiotensin Converting Enzyme Inhibitors, 11, (1998), p. 631-639 (Year: 1998).*
De Simone et al., Should all patients with hypertension have echocardiography?, Journal of Human Hypertension, 14, (2000), p. 417-421 (Year: 2000).*
Yoshikawa et al., Midwall ejection fraction for assessing systolic performance of the hypertrophic left ventricule, Cardiovascular Ultrasound, 10(45), (2012), (7 pages) (Year: 2012).*

(Continued)

*Primary Examiner* — Ellen J Marcsisin
(74) *Attorney, Agent, or Firm* — Stinson LLP

(57) ABSTRACT

The present invention relates to a method for assessing whether a subject shall be subjected to an imaging based diagnostic assessment. The method is based on the determination of the amount(s) of a cardiac Troponin and/or Fibroblast Growth Factor 23 (FGF-23) in a sample from the subject, and on the comparison of the, thus, determined amount(s) with a reference amount (reference amounts). The present invention also relates to a system for performing an assessment whether a subject shall be subjected to an imaging based diagnostic assessment and to reagents and kits used in performing the methods disclosed herein. Moreover, the present invention is directed to a method for predicting the risk of mortality and/or of a cardiovascular event. Also encompassed is a method for diagnosing an early stage of LVH in a subject having a preserved left ventricular ejection.

13 Claims, 2 Drawing Sheets

(56) References Cited

OTHER PUBLICATIONS

De Lemos, James A. et al., Association of Troponin T Detected With a Highly Sensitive Assay and Cardiac Structure and Mortality Risk in the General Population, 2010, pp. 2503-2512, vol. 304, No. 22.

De Simone, Giovanni et al., Assessment of Left Ventricular Function by the Midwall Fractional Shortening/End-Systolic Stress Relation in Human Hypertension, Journal of the American College of Cardiology, May 1994, 1444-1451, vol. 23, No. 6.

Faul, Christian et al., FGF23 induces left ventricular hypertrophy, Journal of Clinical Investigation, 2011, pp. 4393-4408, vol. 121, No. 11.

Fukumoto, Sciji, FGF23-Klotho pathway and cardiovascular diseases, Cardioangiology, 2012, pp. 223-227, vol. 71, No. 3.

Gutiérrez, Orlando M. et al., Fibroblast Growth Factor 23 and Left Ventricular Hypertrophy in Chronic Kidney Disease, 2009, pp. 2545-2553, vol. 119, No. 19.

Heart Failure Society of America, Section 11: Evaluation and Management of Patients with Heart Failure and Preserved Left Ventricular Ejection Fraction, Journal of Cardiac Failure, 2010, pp. e126-e133, vol. 16, No. 6, Elsevier Inc.

International Search Report dated Jun. 27, 2013, in Application No. PCT/EP2013/056706, 9 pages.

Isobe, Kazuya et al., Inhibition of Endostatin/Collagen XVIII Deteriorates Left Ventricular Remodeling and Heart Failure in Rat Myocardial Infarction Model, Circulation Journal, 2010, pp. 109-119, vol. 74.

Ix, Joachim H. et al., Fibroblast Growth Factor-23 and Death, Heart Failure, and Cardiovascular Events in Community-Living Individuals, Journal of the American College of Cardiology, 2012, pp. 200-207, vol. 60, No. 3.

Kendrick, Jessica et al., FGF-23 Associates with Death, Cardiovascular Events, and Initiation of Chronic Dialysis, Journal of the American Society of Nephrology, 2011, pp. 1913-1922, vol. 22, No. 10.

Kirkpantur, Alper et al., Serum fibroblast growth factor-23 (FGF-23) levels are independently associated with left ventricular mass and myocardial performance index in maintenance haemodialysis patients, Nephrology Dialysis and Transplantation, 2011, pp. 1346-1354, vol. 26.

Kitagawa, Masashi et al.., Serum High-Sensitivity Cardiac Troponin T Is a Significant Biomarker of Left-Ventricular Diastolic Dysfunction in Subjects with Non-Diabetic Chronic Kidney Disease, Nephron Extra, 2011, pp. 166-177, vol. 1.

Lang, Roberto M. et al., Recommendations for chamber quantification, European Journal of Echocardiography, 2006, pp. 79-108, vol. 7.

Latini, Roberto et al.., Prognostic Value of Very Low Plasma Concentrations of Troponin T in Patients With Stable Chronic Heart Failure, Circulation, 2007, pp. 1242-1249, vol. 116.

Masson, S. et al., High-sensitivity cardiac troponin T for detection of subtle abnormalities of cardiac phenotype in a general population of elderly individuals, Journal of Internal Medicine, 2013, pp. 306-317, vol. 273, No. 3.

Masson, S. et al., The Fibroblast Growth Factor-23 / vitamin D Axis is Associated with Subtle Alterations in Left Ventricular Mass and Function in an Elderly Population, no date, 2 pages.

Mirza, Majd A. I. et al., Serum intact FGF23 associate with left ventricular mass, hypertrophy and geometry in an alderly population, Atherosclerosis, 2009, pp. 546-551, vol. 207, No. 2.

Mureddu, Gian Francesco et al., Prevalence of preclinical and clinical heart failure in the elderly. A population-based study in Central Italy, European Journal of Heart Failure, 2012, pp. 718-729, vol. 14, No. 7.

Nadir, M. Adnan et al., Improving the Primary Prevention of Cardiovascular Events by Using Biomarkers to Identify Individuals With Silent Heart Disease, Journal of the American College of Cardiology, 2012, pp. 960-968, vol. 50, No. 11.

Negishi, Kazuaki et al., Association Between Fibroblast Growth Factor 23 and Left Ventricular Hypertrophy in Maintenance Hemodialysis Patients-Comparison With B-Type Natriuretic Peptide and Cardiac Troponin T, Circulation Journal, 2010, pp. 2734-2740, vol. 74.

Package Insert, Human FGF-23 (C-Term) ELISA Kit, Immutopics, 2011, 4 pages.

Package Insert, Troponin T hs Cobas, Roche Diagnostics GmbH, Dec. 2008, 5 pages.

Satyan, Sangeetha et al., Relationships of N-Terminal Pro-B-Natriuretic Peptide and Cardiac Troponin T to Left Ventricular Mass and Function and Mortality in Asymptomatic Hemodialysis Patients, American Journal of Kidney Diseases, 2007, pp. 1009-1019, vol. 50, No. 6.

Shimada, Takashi et al., Cloning and characterization of FGF23 as a causative factor of tumor-induced osteomalacia, PNAS, 2001, pp. 6500-6505, vol. 98, No. 11.

Taddei, Stefano et al., Hypertension, left ventricular hypertrophy and chronic kidney disease, Heart Failure Reviews, 2011, pp. 615-620, vol. 16.

Tulevski, Igor I. et al., Combined utility of brain natriuretic peptide and cardiac troponine T may improve rapid triage and risk stratification in normotensive patients with pulmonary embolism, International Journal of Cardiology, 2007, pp. 161-166, vol. 116, No. 2.

Vinch, Craig S. et al., Analysis of Left Ventricular Systolic Function Using Midwall Mechanics in Patients 60 Years of Age With Hypertensive Heart Disease and Heart Failure, American Journal of Cardiology, 2005, pp. 1299-1303, vol. 96, No. 9.

Wang, Angela Yee-Moon et al., Diagnostic potential of serum biomarkers for left ventricular abnormalities in chronic peritoneal dialysis patients, Nephrology Dialysis and Transplantation, 2009, pp. 1962-1969, vol. 24, No. 6.

Hamano, Takayuki, The association between mineral metabolism, cardiovascular mortality, and all-cause mortality, Cardioangiology, 2012, pp. 217-222, vol. 71, No. 3.

Komaba, Hirotaka and Fukugawa, Masafumi, Disturbance of phosphorus metabolism in chronic kidney disease, Clinical Calcium, 2009, pp. 18-24, vol. 19, No. 2, Abstract.

Nakai, Kentaro et al., Hyperphosphatemia and mortality in dialysis and predialysis patients, Kidney and Metabolic Bone Diseases, 2009, pp. 309-316, vol. 22, No. 4, Abstract.

Yeap, Bu B. et al., Associations of IGF1 and IGFBPs 1 and 3 with all-cause and cardiovascular mortality in older men: the Heath In Men Study, European Journal of Endocrinology, 2011, pp. 715-723, vol. 164.

Binder, Lutz et al., N-Terminal Pro-Brain Natriuretic Peptide or Troponin Testing Followed by Echocardiography for Risk Stratification of Acute Pulmonary Embolism, Circulation, 2005, pp. 1573-1579, vol. 112.

López-Bermejo, Abel et al., Generation of Anti-Insulin-Like Growth Factor-Binding Protein-Related Protein 1 (IGFBP-rP1/MAC25) Monoclonal Antibodies and Immunoassay: Quantification of IGFBP-rP1 in Human Serum and Distribution in Human Fluids and Tissues, The Journal of Clinical Endocrinology & Metabolism, 2003, pp. 3401-3408, vol. 88, No. 7.

López-Bermejo, Abel et al., Insulin Resistance Is Associated With Increased Serum Concentration of IGF-Binding Protein-Related Protein 1 (IGFBP-rP1/MAC25), Diabetes, 2006, pp. 2333-2339, vol. 55.

Inosaka, Yoshitaka, Relation between FGF23 value of serum in storage period and CVD event during, before, and after dialysis, Journal of Japanese Society for Dialysis Therapy, 2012, p. 350, vol. 45, Supplement 1, SY-5-1.

Kato, Hideki, A chronic kidney disease and phosphate metabolism, Annual Review of Kidney, 2012, pp. 171-177.

Suzuki, Masashi, What is FGF23 Responsible For?, Quarterly Journal of Dialysis, 2010, pp. 25-26, vol. 20, No. 3.

* cited by examiner

ASSESSING WHETHER A SUBJECT SHALL BE SUBJECTED TO IMAGING BASED DIAGNOSTIC

CROSS REFERENCE TO RELATED APPLICATIONS

This application is a continuation of U.S. application Ser. No. 14/644,695 filed Mar. 11, 2015, which is a continuation of International Patent Application PCT/EP2013/056706 filed Mar. 28, 2013, and claims priority to EP Patent Application No. 12184085.4 filed Sep. 12, 2012, the disclosures of which are hereby incorporated by reference in their entirety.

SUMMARY OF THE INVENTION

The present invention relates to a method for assessing whether a subject shall be subjected to an imaging based diagnostic assessment. The method is based on the determination of the amount(s) of a cardiac Troponin and/or Fibroblast Growth Factor 23 (FGF-23) in a sample from the subject, and on the comparison of the, thus, determined amount(s) with a reference amount (reference amounts). The present invention also relates to a system for performing an assessment whether a subject shall be subjected to an imaging based diagnostic assessment and to reagents and kits used in performing the methods disclosed herein. Moreover, the present invention is directed to a method for predicting the risk of mortality and/or of a cardiovascular event. Also encompassed is a method for diagnosing an early stage of LVH in a subject having a preserved left ventricular ejection.

Abnormal midwall fractional shortening (MFS) marks abnormal systolic and/or diastolic ventricular function at an early pre-clinical stage during the progression to left ventricular hypertrophy (LVH) and heart failure as well as in myocardial ischemia. MFS is a measure of systolic function that identifies hypertensive patients who have evidence of target-organ damage, impaired contractile reserve, and increased mortality. Therefore, the identification of subjects with abnormal fractional shortening is important. In particular, the identification allows for initiating appropriate preventive treatment before non-reversible progression of left ventricular hypertrophy or even heart failure occurs.

Fractional shortening can be recognized by using imaging modalities (see e.g. Honda T et al. J Cardiol, 2002 March; 39(3):141-50; Palmiero P et al. Echocardiography. 2008 January; 25{1}:20-6; Shimizu G et al. Circulation. 1985; 71:266-272). However, abnormal midwall fractional shortening is frequently not tested or overlooked. This holds true in particular in the elderly. Assessment of fractional shortening using echocardiography requires expensive instrumentation, specialized imaging techniques, and expert image recording and interpreting skills. Widespread application of echocardiographic screening for abnormal MFS has been limited by cost-to-benefit consideration. This disadvantage, however, could be overcome using a blood biomarker associated with midwall fractional shortening.

Furthermore a biomarker based method would be useful to stratify patients for subsequent imaging techniques such as echocardiography or magnetic resonance imaging.

WO 2012/025355 describes a method of diagnosing functional and/or structural abnormalities of the heart preceding heart failure, in a subject bearing risk factors of developing heart failure by determining the amount of a cardiac troponin and of IGFBP7. It discloses that a level of Troponin T of equal to or larger than 3.5 pg/ml is indicative for functional and/or structural abnormalities of the heart preceding heart failure. Subjects with midwall fractional shortening (MFS)<15% are not described.

Saytan et al. 2007 (Am J Kidney Dis. December; 50(6): 1009-1019) discloses that low midwall fractional shortening is a measure of poor systolic function systolic function and that in asymptomatic hemodialysis patients low midwall fractional shortening was an independent correlate of log NT-proBNP (p<0.01). Moreover, there was no significant correlation between cTnT and mWFS (p=0.51).

Kitagawa et al. 2011 (Nephron Extra 1(1): 166-177) discloses that BNP as well as hs troponin I can be used to detect left ventricular diastolic dysfunction in non-diabetic chronic kidney disease patients.

The fibroblast growth factor-23 (FGF-23) is a 32 kDa hormone secreted into blood from bone osteocytes. Its two functions are to induce urinary phosphorous excretion and to inhibit activation of Vitamin D; both actions occur in the renal proximale tubule. High concentrations of circulating FGF-23 are found in patients with end-stage renal disease. The hormone is a key player in the regulation of calcium-phosphate and vitamin D metabolism and has a causal role in the pathogenesis of LV hypertrophy, a major determinant of cardiovascular events.

Kirkpantur et al. 2011 (Nephrol Dial Transplant 26: 1346-1354) disclose that FGF-23 levels are associated with increased left ventricular mass index (LVMI) and myocardial performance index in dialysis patients (See Table 2). Subjects with abnormal fraction shortening<15% were not examined (see Table 2; all subjects with FS=fractional shortening of around 30%).

Mirzaa et al. 2009 (Mirzaa Atheroscleosis 207, 546-551) disclose an association between elevated serum FGF-23 levels and increased left ventricular mass, left ventricular hypertrophy and left ventricular geometric shape and increased risk for the presence of left ventricular hypertrophy in elderly subject which is more pronounced in patients with renal diseases (eGFR<60 mL/min).

Faul et al. 2011 (J Clin Invest 121(11): 4393-4408) examined the causal role for FGF-23 in the pathogenesis of LVH in animal models and suggests that chronically elevated FGF-23 levels contribute directly to high rates of left ventricular hypertrophy and mortality. It also discloses an association between elevated serum FGF-23 levels and prevalence of left ventricular hypertrophy in humans and that increased FGF-23 levels precede development of left ventricular hypertrophy in humans with chronic kidney disease. Also described is a method of predicting the risk of a patient to suffer from left ventricular hypertrophy in the future based on the detection of FGF-23.

Gutierrez et al. 2009 (Circulation May 19; 119(19): 2545-2552) discloses that FGF-23 concentrations were significantly associated with increased LVMI. Increasing log FGF-23 concentrations were also significantly associated with the presence of left ventricular hypertrophy.

Taddei et al. 2011 (Heart Fail Rev 16:615-620) discloses vitamin D deficiency, i.e. reduced vitamin D levels, as a risk factors for LVH in chronic kidney disease patients.

Palmiero et al. 2008 (Echocardiography January; 25(1): 20-6) discloses that midwall fractional shortening is an important early sign of ventricular dysfunction in hypertensive patients, even when diastolic function is normal.

Ix et al. 2012 (J Am College of Cardiol.) disclose, that FGF-23 may be used as predictor in community subjects.

The IGFBP system plays an important role in cell growth and differentiation. IGF binding protein 7 (=IGFBP-7) is a 30-kDa modular glycoprotein known to be secreted by endothelial cells, vascular smooth muscle cells, fibroblasts, and epithelial cells (Ono, Y., et al., Biochem Biophys Res Comm 202 (1994) 1490-1496). In the literature this molecule has also been denominated as FSTL2; IBP 7; IGF binding protein related protein I; IGFBP 7; IGFBP 7v; IGFBP rP1; IGFBP7; IGFBPRP1; insulin like growth factor binding protein 7; insulin like growth factor binding protein 7 precursor; MAC25; MAC25 protein; PGI2 stimulating factor; and PSF or Prostacyclin stimulating factor. Low levels of IGFB-7 were detected in random human sera and increased serum levels have been seen in association with insulin-resistance (Lopez-Bermejo, A., et al., J. Clinical Endocrinology and Metabolism 88 (2003) 3401-3408, Lopez-Bermejo, A., et al., Diabetes 55 (2006) 2333-2339).

US2010/0285491 discloses the use of IGFBP-7 in the assessment of heart failure. It further discloses that the marker IGFBP-7 can be used for selecting a treatment regimen for a patient suffering from HF.

Motiwala et al. disclose that serial measurement of IGFBP7 may be used as predictor in patients with left ventricular systolic dysfunction (JACC, 2013, 61(10), E565).

Mimecan (frequently also referred to as "osteoglycin") is a multifunctional component of the extracellular matrix. Mimecan has been shown to be involved in regulating collagen fibrillogenesis, a process essential in development, tissue repair, and metastasis (Tasheva et al., MoI. Vis. 8 (2002) 407-415). It plays a role in bone formation in conjunction with TGF-beta-1 or TGF-beta-2. Transcriptome analyses in rat and human heart tissue revealed a high correlation of mimecan with left ventricular mass as well as with extracellular remodelling in dilatative cardiomyopathy (Petretto, E. et al., Nature Genetics 40 (2008) 546-552.

WO2011/012268 discloses that mimecan can be used as a marker for the assessment of heart failure.

Endostatin was originally isolated from murine hemangioendothelioma as a 20 kDA proteolytic fragment of type XVIII collagen (O'Reilly, M. S. et al., Cell 88 (1997) 277-285). Collagens represent a family of extracellular matrix proteins with a characteristic triple-helical conformation forming supra-molecular aggregates that play a dominant role in maintaining tissue structural integrity. Excessive collagen deposition leads to fibrosis disrupting the normal functioning of surrounding tissues. Endostatin is released from the alpha 1 chain of collagen XVIII by action of various proteolytic enzymes (Ortega, N. and Werb, Z., Journal of Cell Science 115 (2002) 4201-4214). Endostatin is a potent inhibitor of angiogenesis and blood vessel growth.

WO2010/124821 discloses that endostatin can be used as a marker for the assessment of heart failure.

The technical problem underlying the present invention can be seen as the provision of means and methods for complying with the aforementioned needs.

DETAILED DESCRIPTION

Figure 1A:
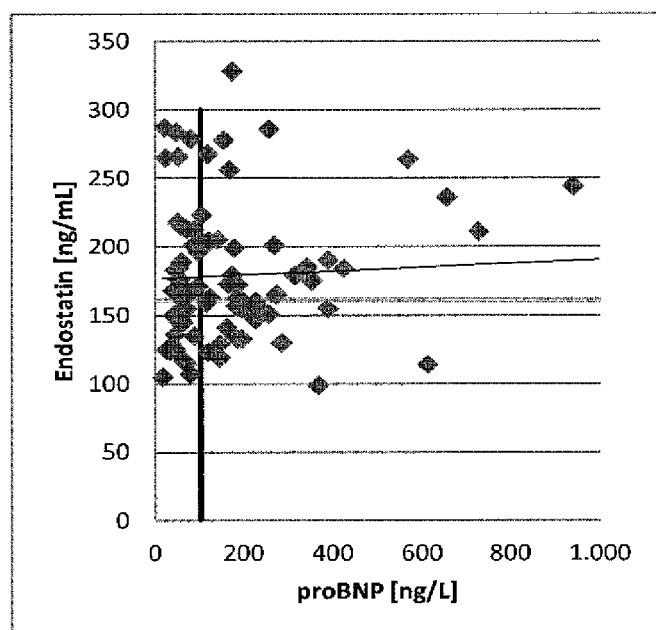
FIG. 1A: Endostatin and NT-ProBNP levels in female subjects with borderline LVH/mildly elevated LV masses.

The technical problem is solved by the embodiments characterized in the claims and herein below.

Method for Assessing Whether a Subject Shall be Subjected to an Imaging Based Diagnostic Assessment The present invention relates to a method for assessing whether a subject shall be subjected to an imaging based diagnostic assessment comprising the steps of
  a) determining the amount(s) of a cardiac Troponin and/or Fibroblast Growth Factor 23 (FGF-23) in a sample from the subject, and
  b) comparing the, thus, determined amount(s) to a reference amount (reference amounts), whereby it is assessed whether the subject shall be subjected to an imaging based diagnostic assessment.

Preferably, it is assessed whether the subject shall be subjected to an imaging based diagnostic assessment by carrying out the further step of c) assessing whether the subject shall be subjected to an imaging based diagnostic assessment, based on the results of the comparison carried out in step b).

The method of the present invention, preferably, is an ex vivo or in vitro method. Moreover, it may comprise steps in addition to those explicitly mentioned above. For example, further steps may relate to sample pre-treatments or evaluation of the results obtained by the method. The method may be carried out manually or assisted by automation. Preferably, step (a) and/or (b) may in total or in part be assisted by automation, e.g., by a suitable robotic and sensory equipment for the determination in step (a) or a computer-implemented comparison and/or assessment based on said comparison in step (b).

Accordingly, the present invention also preferably relates to a system for assessing whether a subject shall be subjected to an imaging based diagnostic assessment, comprising
  a) an analyzer unit configured to contact, in vitro, a portion of a sample from a subject with a ligand comprising specific binding affinity for a cardiac Troponin, and/or with a ligand comprising specific binding affinity for FGF-23,
  b) an analyzer unit configured to detect a signal from the portion of the sample from the subject contacted with the ligand(s),
  c) a computing device having a processor and in operable communication with said analysis units, and
  d) a non-transient machine readable media including a plurality of instruction executable by a the processor, the instructions, when executed calculate the amount(s) of the cardiac Troponin and/or FGF-23, and compare the amount(s) with a reference amount (reference amounts), thereby assessing whether the subject shall be subjected to an imaging based diagnostic assessment.

The term "assessing" as used herein means to determine whether a subject as set forth herein shall be subjected to an imaging based diagnostic assessment, or not. Thus, by carrying out the method of the present invention, it can be stratified whether a subject as set forth herein should be subjected to imaging based diagnostic assessment, or not. By carrying out the method of the present invention, e.g., subjects can be identified which should not be subjected to these diagnostic assessments. Since these assessments require expensive instrumentation, specialized imaging techniques, and expert image recording and interpreting skills, unnecessary health care expenses can be avoided. A subject who is susceptible to an imaging based assessment, preferably, is a subject who has an increased probability to suffer from systolic and/or diastolic dysfunction. Thus, the subject requires an imaging based diagnostic assessment. In particular, a subject who is susceptible to an imaging based assessment, preferably, is a subject who has an increased probability to suffer from abnormal midwall fractional shortening. A subject who is not susceptible to an imaging based assessment, preferably, is a subject who has a reduced probability to suffer from systolic and/or diastolic dysfunction. Thus, the subject does not require an imaging based diagnostic assessment. In particular, a subject who is not susceptible to an imaging based assessment, preferably, is a subject who has a reduced probability to suffer from abnormal midwall fractional shortening.

As will be understood by those skilled in the art, such an assessment is usually not intended to be correct for 100% of the subjects to be assessed. The term, however, requires that a statistically significant portion of subjects can be correctly assessed. Whether an assessment is correct can be confirmed by methods well known in the art. Moreover, whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001.

In accordance with the method of the present invention, it shall be assessed whether the subject to be tested shall be subjected to an imaging based diagnostic assessment. Preferably, the imaging based diagnostic assessment aims to create pictures of the heart. Thus, the assessment shall be an assessment of the heart. More preferably, the imaging based diagnostic assessment is echocardiography or magnetic resonance imaging (MRI). The most preferred diagnostic assessment is echocardiography.

The aforementioned imaging techniques are well known in the art. The term "echocardiography" as used herein, preferably, refers to the evaluation of cardiac structure and function with images and recordings produced by ultrasound. Preferably, the term includes one dimensional, two dimensional and three dimensional echocardiography. Further, it is envisaged that the term "echocardiography" includes transthoracic echocardiography, stress echocardiography, and contrast echocardiography. In a particularly preferred embodiment, the echocardiography is M Mode echocardiography.

Magnetic resonance imaging is a medical imaging technique used in radiology to visualize internal structures of the body in detail. By MRI, the absorption and transmission of high-frequency radio waves are analyzed as they irradiate the hydrogen atoms in water molecules and other tissue components placed in a strong magnetic field. The term "magnetic resonance imaging" as used herein refers to cardiac magnetic resonance imaging (frequently also referred to as cardiovascular magnetic resonance imaging).

In a preferred embodiment of the method of the present invention, the imaging based diagnostic assessment is used for diagnosing diastolic dysfunction. In a even more preferred embodiment of the method of the present invention, the imaging based diagnostic assessment is used for diagnosing systolic dysfunction.

The term "diastolic dysfunction" is well understood by the skilled person. Preferably, the term refers to a reduced pump function of the heart due to impaired ventricular filling. Thus, the term, preferably, refers to decline in performance of one or both ventricles of the heart during the time phase of diastole. The term "systolic dysfunction" is also well known in the art. As used herein, the term preferably refers to a reduced pump function of the heart due to a decreased contractility of the ventricle. Preferably, the systolic and/or diastolic dysfunction is not accompanied by overt signs of heart failure. Also preferably, the systolic and/or diastolic dysfunction shall not be accompanied by left ventricular hypertrophy.

In a particularly preferred embodiment of the method of the present invention, the imaging based diagnostic assessment is used for diagnosing abnormal midwall fractional shortening, in particular abnormal left ventricular midwall fractional shortening.

The expression "midwall fractional shortening" is well known in art (abbreviated herein as "MFS". It is well known in the art that reduced left ventricular (LV) MFS is an early sign of LV dysfunction is reduced LV midwall fractional shortening. Preferably, midwall fractional shortening is considered as abnormal, if it is lower than 15%. This cut-off point has been used as a reference value in the setting of HF and has demonstrated prognostic relevance in hypertensive subjects (see Murredu et al., European Journal of Heart Failure (2012) 14, 718-729). Also preferably, midwall fractional shortening is considered as abnormal, if it is lower than 14%, or 13%. Further, midwall fractional shortening is considered as normal, if it is larger than (or equal to) 15%. Also preferably, midwall fractional shortening is considered as normal, if it is larger than 16%, or 17%.

Midwall fractional shortening can be calculated by well-known methods. For example, it may be calculated from the two-shell cylindrical model as described by Shimizu et al. which is herewith incorporated by reference with respect to its entire disclosure content (Shimizu G, Hirota Y, Kita Y, Kawamura K, Saito T, Gaasch W H. Left ventricular midwall mechanics in systemic arterial hypertension. Circulation 1991; 83:1676-84)). This method is a refinement of the conventional midwall method and provides data that reflect shortening of a theoretic circumferential midwall fiber or ring of myocardium. It assumes a constant left ventricular mass throughout the cardiac cycle and does not require the assumption that inner and outer wall thickening fractions are equal.

The determination of MFS is also described by Mayet et al. or in earlier papers from Shimizu et al. all of which are herewith incorporated by reference. (see e.g. Mayet et al., Hypertension. 2000; 36: 755-759; Shimizu G, Zile M R, Blaustein A S, Gaasch W H. Left ventricular chamber filling and midwall fiber lengthening in patients with left ventricular hypertrophy: overestimation of fiber velocities by conventional midwall measurements. Circulation. 1985; 71:266-272, or Shimizu G, Conrad C H, Gaasch W H. Phase-plane analysis of left ventricular chamber filling and midwall fiber lengthening in patients with left ventricular hypertrophy. Circulation. 1987; 75(suppl I):I-34-I-39). Moreover, the determination of MFS has been described by de Simone et al. (JACC, 1994, Vol. 23(6): 1444-51) which is also incorporated by reference in its entirety. Preferably, MFS as used herein is determined according to the method as described by Shimizu in 1987 and 1985, more preferably MFS is determined according to Mayet et al., most preferably, MFS is determined according to de Simone.

The term "subject" as used herein relates to animals, preferably mammals, and, more preferably, humans. The subject in the context of the present invention may be male or female. Further, it is particularly envisaged that the subject is older than 65 years.

In a preferred embodiment of the present invention, the subject does not suffer from left ventricular hypertrophy. In particular, it is particularly envisaged that the subject has a normal left ventricular mass.

The term "left ventricular hypertrophy" is well known in the art. A detailed overview on left ventricular hypertrophy can be, e.g. found in standard text books (see Swamy Curr Cardiol Rep (2010) 12:277-282). LVH can be detected by electrocardiography, echocardiography, or cardiac magnetic resonance imaging (MRI). Preferably, LVH is detected by echocardiography. Moreover, criteria for the diagnosis of LVH are well known in the art (Mancia et al., European Heart J. 2007, 28: 1462, Die Innere Medizin: Referenzwerk für den Facharzt-Wolfgang Gerok—2007, page 293, Swamy Curr Cardiol Rep (2010) 12:277-282).

The assessment LVH, preferably, includes measurements of the septum diameter, left ventricular posterial wall thickness and end diastolic diameter, with calculation of left ventricular mass according to formulae known in the art. Particularly preferred criteria for diagnosing LVH are e.g. disclosed in the guidelines (Mancia et al., European Heart J. 2007, 28: 1462). Also preferably, the criteria may be taken from the ACC/AHA guidelines for the evaluation and management of chronic heart failure in the adult, J. Am. Coll. Cardiol. 2001; 38; 2101-2113.

Preferably, the Cornell voltage criteria, the Cornell product criteria, the Sokolow-Lyon voltage criteria or the Romhilt-Estes point score system is/are used (Mancia et al., European Heart J. 2007, 28: 1462).

The term "left ventricular hypertrophy" (abbreviated "LVH") as used herein, preferably, relates to a thickening of the walls of the ventricles. LVH is, preferably, a response to a chronically increased workload on the heart. LVH found in patients suffering from arterial hypertension (i.e. high blood pressure) is a disease requiring treatment. In the context of the present invention functional and/or structural abnormalities of the heart typically precedes left ventricular hypertrophy and/or heart failure.

Hypertrophy as a response to the increased afterload associated with elevated systemic vascular resistance is necessary and protective up to a certain point. Beyond that point, a variety of dysfunctions accompany LVH, including lower coronary vasodilatory capacity, depressed left ventricular wall mechanics, and abnormal left ventricular diastolic filling pattern.

Preferably, a male subject suffers from LVH if the left ventricular mass index (and, thus, the ratio of the left ventricular mass to body surface, abbreviated LVMI) is larger than 105 g/m$^2$, more preferably, is larger than 110 g/m$^2$, and most preferably, is larger than 115 g/m$^2$ (or in particular larger than 116 g/m$^2$). Preferably, a female subject suffers from LVH, if the LVMI is larger than 85 g/m$^2$, even more preferably, is larger than 90 g/m$^2$, and most preferably, is larger than 96 g/m$^2$.

As set forth herein above, the subject, preferably, shall have a normal left ventricular mass. If the subject is male, the following applies: a subject is considered to have a normal left ventricular mass, if the left ventricular mass index of the male subject is, preferably, equal to or lower than 105 g/m$^2$, or, more preferably, is equal to or lower than 110 g/m$^2$, or, most preferably, is equal to or lower than 115 g/m$^2$ (or in particular equal to or lower than 116 g/m$^2$). If the subject is female, the following applies: a subject is considered to have a normal left ventricular mass, if the left ventricular mass index of the subject is, preferably, equal to or lower than 85 g/m$^2$, or, more preferably, is equal to or lower than 90 g/m$^2$, or, most preferably, is equal to or lower than 96 g/m$^2$. It is to be understood that a subject who has a normal left ventricular mass does not suffer from LVH.

Preferably, the LVMI is determined as disclosed by Lang et al. (Recommendations for chamber quantification. Eur J Echocardiogr 2006; 7:79-108).

In a preferred embodiment of the present invention, the subject suffers from hypertension. The hypertension can be any form of hypertension known to the person skilled in the art. In a preferred embodiment of the present invention, the individual suffers from arterial hypertension, systolic and/and or diastolic hypertension. In particular, the subject shall suffer from arterial hypertension. Preferably, a subject suffers from arterial hypertension, if systolic pressure exceeds 140 mmHg and/or the diastolic pressure exceeds 90 mmHg More preferably, a subject suffers from arterial hypertension, if systolic pressure exceeds 140 mmHg and/or the diastolic pressure exceeds 90 mmHg for three months or more, six months or more, twelve months or more, two years or more, three years or more, or five years or more. Preferably, temporary elevated blood pressure, e.g., caused by physical exercise, is not encompassed by the term "arterial hypertension".

Hypertension may be accompanied by risk factors for developing heart failure. Preferred risk factors for developing heart failure, subclinical organ damage, e.g. of the heart, brain, kidneys, blood vessels; obesity, preferably obesity defined as body mass index BMI<25 kg/m$^2$; adipositas; metabolic syndrome; diabetes mellitus type 1 or type 2, in particular type 2 diabetes mellitus; type 1 diabetes with microalbuminuria, cigarette smoking; history of revascularization; history of cardiotoxic drug therapy or alcohol abuse; dyslipidemia; total cholesterol, total cholesterol/HDL-cholesterol ratio, personal history of rheumatic fever; family history of cardiomyopathy. Thus, the may suffer from hypertension accompanied by one or more of the above-referenced further risk factors. However, it is also contemplated that said subject suffers from hypertension alone.

Moreover, it is further envisaged that the subject does not suffer from ACS (acute coronary syndrome). The term "ACS" as used herein includes STEMI (ST-elevation myocardial infarction); NSTEMI (non ST-elevation myocardial infarction) and unstable angina pectoris. It is further envisaged that the subject to be tested does not have a history of ACS. In particular, the subject shall not have suffered from ACS within one month prior to carrying out the method of the present invention (to be more precise, within one month prior to obtaining the sample).

It is also contemplated that the subject does not suffer from coronary artery disease. The term "coronary artery disease", abbreviated CAD, frequently also called coronary heart disease (CHD) or atherosclerotic heart disease, is known to the person skilled in the art. Preferably, the term refers to a condition in which the blood vessels that supply blood and oxygen to the heart are narrowed. Coronary artery disease is usually caused by a condition called atherosclerosis, which occurs when fatty material and a substance called plaque builds up on the walls of your arteries. This causes them to get narrow. Particularly, CAD is the result of the accumulation of atheromatous plaques within the walls of the arteries that supply the myocardium (the muscle of the heart). Preferably, a subject who suffers from CAD has at least 50% stenosis (and thus at least 50% occlusion), in at least one major coronary artery. Thus, a subject who does not suffer from CAD, preferably, has less than 50% steonis in the major coronary arteries. How to assess the degree of occlusion of a coronary artery is well known in the art, preferably, the degree is assessed by coronary angiography. While the symptoms and signs of coronary artery disease are noted in the advanced state of disease, most individuals with coronary artery disease show no evidence of disease for decades as the disease progresses before the first onset of symptoms of an acute event, often a "sudden" heart attack, finally arise.

Further, the subject shall not be pregnant. Also, the subject is, preferably, not an athlete.

It is further envisaged that the subject does not suffer from heart failure and/or does not show overt symptoms of heart failure.

The term "heart failure" as used herein, preferably, relates to an impaired systolic and/or diastolic function of the heart being accompanied by overt signs of heart failure as known to the person skilled in the art. Preferably, heart failure referred to herein is also chronic heart failure. Heart failure according to the present invention includes overt and/or advanced heart failure. In overt heart failure, the subject shows symptoms of heart failure as known to the person skilled in the art. It is particularly contemplated that the term "heart failure" as used herein refers to stages C and D of the ACC/AHA classification. In these stages, the subject shows typical symptoms of heart failure, i.e. the subject is not apparently healthy. The subject having heart failure and being classified into stage C or D has undergone permanent, non reversible structural and/or functional changes to his myocardium, and as a consequence of these changes, full health restoration is not possible.

The ACC/AHA classification is a classification for heart failure developed by the American College of Cardiology and the American Heart Association (see J. Am. Coll. Cardiol. 2001; 38; 2101-2113, updated in 2005, see J. Am. Coll. Cardiol. 2005; 46; e1-e82). 4 stages A, B, C and D are defined. Stages A and B are not HF (heart failure) but are considered to help identify patients early before developing "truly" HF. Stages A and B patients are best defined as those with risk factors for the development of HF. For example, patients with coronary artery disease, hypertension, or diabetes mellitus who do not yet demonstrate impaired left ventricular (LV) function, hypertrophy, or geometric chamber distortion would be considered stage A, whereas patients who are asymptomatic but demonstrate LV hypertrophy (LVH, a phenomenon in which the walls of the ventricles thicken) and/or impaired LV function would be designated as stage B. Stage C then denotes patients with current or past symptoms of HF associated with underlying structural heart disease (the bulk of patients with HF), and stage D designates patients with truly refractory HF.

In a preferred embodiment of the present invention, the subject to be tested is classified as stage B subject (according to the ACC/AHA classification as referred to above). Thus, the subject does not show overt signs of heart failure. If the subject is classified as stage B subject, the subject, preferably, has a normal left ventricular mass as specified elsewhere in herein in more detail.

Further, it is envisaged that the subject in the context of the present invention does not have impaired renal function. Preferably, the subject shall not suffer from renal failure, in particular the subject shall not suffer from acute, chronic and/or end stage renal failure. Further, the subject, preferably, shall not suffer from renal hypertension. How to assess whether a subject exhibits impaired renal function is well known in the art. Renal disorders can be diagnosed by any means known and deemed appropriate. Particularly, renal function can be assessed by means of the glomerular filtration rate (GFR). For example, the GFR may be calculated by the Cockgroft-Gault or the MDRD formula (Levey 1999, Annals of Internal Medicine, 461-470). GFR is the volume of fluid filtered from the renal glomerular capillaries into the Bowman's capsule per unit time. Clinically, this is often used to determine renal function. The GFR was originally estimated (the GFR can never be determined, all calculations derived from formulas such as the Cockgroft Gault formula of the MDRD formula deliver only estimates and not the "real" GFR) by injecting inulin into the plasma. Since inulin is not reabsorbed by the kidney after glomerular filtration, its rate of excretion is directly proportional to the rate of filtration of water and solutes across the glomerular filter. In clinical practice however, creatinine clearance is used to measure GFR. Creatinine is an endogenous molecule, synthesized in the body, which is freely filtered by the glomerulus (but also secreted by the renal tubules in very small amounts). Creatinine clearance (CrCl) is therefore a close approximation of the GFR. The GFR is typically recorded in milliliters per minute (mL/min). The normal range of GFR for males is 97 to 137 mL/min, the normal range of GFR for females is 88 to 128 ml/min Thus, it is particularly contemplated that the GFR of a subject who does not exhibit impaired renal function is within this range. Moreover, said subject preferably, has a blood creatinine level (in particular a serum creatinine level) of lower than 0.9 mg/dl, more preferably of lower than 1.1 mg/dl and most preferably of lower than 1.3 mg/dl.

If the method of the present invention encompasses the determination of the amount of FGF-23 (and vitamin D), the subject, preferably, shall not exhibit vitamin D deficiency.

Moreover, it is preferred that the subject in the context of the method for assessing whether a subject shall be subjected to an imaging based diagnostic assessment, the method for diagnosing abnormal MFS, and the method for predicting the risk of mortality does not have increased levels of a natriuretic peptide. Preferably, the subject does not have increased levels of a brain natriuretic peptide. More preferably, the subject does not have increased levels of a BNP-type natriuretic peptide. Most preferably, the subject does not have increased levels of NT-proBNP. Preferably, the subject has an NT-proBNP level of lower than 125 pg/ml for age<75 years, 450 pg/ml for age≥75 years, or more preferably, of lower than 100 pg/ml for age<75 years, 300 pg/ml for age>=75 years, in particular in a blood, serum or plasma sample.

The term "sample" refers to a sample of a body fluid, to a sample of separated cells or to a sample from a tissue or an organ. Samples of body fluids can be obtained by well known techniques and include, preferably, samples of blood, plasma, serum, or urine, more preferably, samples of blood, plasma or serum. Tissue or organ samples may be obtained from any tissue or organ by, e.g., biopsy. Separated cells may be obtained from the body fluids or the tissues or organs by separating techniques such as centrifugation or cell sorting. Preferably, cell-, tissue- or organ samples are obtained from those cells, tissues or organs which express or produce the peptides referred to herein.

The term "cardiac Troponin" refers to all Troponin isoforms expressed in cells of the heart and, preferably, the subendocardial cells. These isoforms are well characterized in the art as described, e.g., in Anderson 1995, Circulation Research, vol. 76, no. 4: 681-686 and Ferrieres 1998, Clinical Chemistry, 44: 487-493. Preferably, cardiac Troponin refers to Troponin T and/or Troponin I, and, most preferably, to Troponin T. It is to be understood that isoforms of Troponins may be determined in the method of the present invention together, i.e. simultaneously or sequentially, or individually, i.e. without determining the other isoform at all Amino acid sequences for human Troponin T and human Troponin I are disclosed in Anderson, loc cit and Ferrieres 1998, Clinical Chemistry, 44: 487-493.

The term "cardiac Troponin" encompasses also variants of the aforementioned specific Troponins, i.e., preferably, of Troponin I, and more preferably, of Troponin T. Such variants have at least the same essential biological and immunological properties as the specific cardiac Troponins. In particular, they share the same essential biological and immunological properties if they are detectable by the same specific assays referred to in this specification, e.g., by ELISA Assays using polyclonal or monoclonal antibodies specifically recognizing the said cardiac Troponins. Moreover, it is to be understood that a variant as referred to in accordance with the present invention shall have an amino acid sequence which differs due to at least one amino acid substitution, deletion and/or addition wherein the amino acid sequence of the variant is still, preferably, at least about 50%, at least about 60%, at least about 70%, at least about 80%, at least about 85%, at least about 90%, at least about 92%, at least about 95%, at least about 97%, at least about 98%, or at least about 99% identical with the amino sequence of the specific Troponin (in particular over the entire length). Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants may be allelic variants or any other species specific homologs, paralogs, or orthologs. Moreover, the variants referred to herein include fragments of the specific cardiac Troponins or the aforementioned types of variants as long as these fragments have the essential immunological and biological properties as referred to above. Preferably, the cardiac troponin variants have immunological properties (i.e. epitope composition) comparable to those of human troponin T or troponin I. Thus, the variants shall be recognizable by the aforementioned means or ligands used for determination of the concentration of the cardiac troponins.

Thus, the variants shall be recognizable by the aforementioned means or ligands used for determination of the concentration of the cardiac troponins. Such fragments may be, e.g., degradation products of the Troponins. Further included are variants which differ due to posttranslational modifications such as phosphorylation or myristylation. Preferably the biological property of troponin I and its variant is the ability to inhibit actomyosin ATPase or to inhibit angiogenesis in vivo and in vitro, which may e.g. be detected based on the assay described by Moses et al. 1999 PNAS USA 96 (6): 2645-2650). Preferably the biological property of troponin T and its variant is the ability to form a complex with troponin C and I, to bind calcium ions or to bind to tropomyosin, preferably if present as a complex of troponin C, I and T or a complex formed by troponin C, troponin I and a variant of troponin T. It is known that low concentrations of circulating cardiac troponin may be detected in subjects at various conditions, but further studies are required to understand their respective role and rate (Masson et al., Curr Heart Fail Rep (2010) 7:15-21).

Preferably, the cardiac Troponin is Troponin T, in particular human Troponin T. Preferably, the amount of Troponin T is determined by using an high sensitive Troponin assays as described in the Examples, or in WO2012/025355.

The fibroblast growth factor-23 (abbreviated "FGF-23") is a key player in the regulation of cal-cium-phosphate and vitamin D metabolism and has a causal role in the pathogenesis of LV hypertrophy, a major determinant of cardiovascular events. The fibroblast growth factor-23 (FGF-23) is a 32 kDa hormone secreted into blood from bone osteocytes. Its two functions are to induce urinary phosphorous excretion and to inhibit activation of Vitamin D; both actions occur in the renal proximale tubule. High concentrations of circulating FGF-23 are found in patients with end-stage renal disease. Preferably, FGF-23 is human FGF-23. The sequence of human FGF-23 is well known in the art, e.g. the amino sequence can be assessed via GenBank accession number NM_020638.1 GI:10190673. Moreover, the sequence is also disclosed in Shimada et al., 2001, PNAS, vol. 98(11) page 6500 to 6505. The term "FGF-23" encompasses also variants of the aforementioned FGF-23. Such variants have at least the same essential biological and immunological properties as the specific FGF-23. In particular, they share the same essential biological and immunological properties if they are detectable by the same specific assays referred to in this specification, e.g., by ELISA Assays using polyclonal or monoclonal antibodies specifically recognizing the said FGF-23. Moreover, it is to be understood that a variant as referred to in accordance with the present invention shall have an amino acid sequence which differs due to at least one amino acid substitution, deletion and/or addition wherein the amino acid sequence of the variant is still, preferably, at least about 50%, at least about 60%, at least about 70%, at least about 80%, at least about 85%, at least about 90%, at least about 92%, at least about 95%, at least about 97%, at least about 98%, or at least about 99% identical with the amino sequence of the FGF-23 (in particular over the entire length). How to calculate the degree of identity is disclosed elsewhere herein. Preferably, FGF-23 is determined by using the Human FGF-23 (C-term) ELISA Kit from Immutopics, Inc. (which is e.g. distributed under cat. no. 60-6100).

Determining the amount of a peptide or polypeptide, in particular of a marker selected from the group consisting of a cardiac Troponin, Fibroblast Growth Factor 23 (FGF-23), IGFBP7 (IGF binding protein 7), GDF-15, endostatin and mimecan, referred to in this specification relates to measuring the amount or concentration, preferably, semi-quantitatively or quantitatively. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

In accordance with the present invention, determining the amount of a peptide or polypep-tide can be achieved by all known means for determining the amount of a peptide in a sample. Said means comprise immunoassay and methods which may utilize labeled mole-cules in various sandwich, competition, or other assay formats. Such assays are, preferably, based on detection agents such as antibodies which specifically recognize the peptide or polypeptide to be determined. The detection agents shall be either directly or indirectly capable of generating a signal indicating the presence or absence of the peptide or polypep-tide. Moreover, the signal strength can, preferably, be correlated directly or indirectly (e.g. reverse-proportional) to the amount of polypeptide present in a sample. Further suitable methods comprise measuring a physical or chemical property specific for the peptide or polypeptide such as its precise molecular mass or NMR spectrum. Said methods comprise, preferably, biosensors, optical devices coupled to immunoassays, biochips, analytical de-vices such as mass-spectrometers, NMR-analyzers, or chromatography devices. Further, methods include micro-plate ELISA-based methods, fully-automated or robotic immuno-assays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

Preferably, determining the amount of a peptide or polypeptide comprises the steps of (a) contacting a cell capable of eliciting a cellular response the intensity of which is indicative of the amount of the peptide or polypeptide with the said peptide or polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the amount of the peptide or polypeptide.

Also preferably, determining the amount of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spec-trum specific for the pep-tide or polypeptide.

Determining the amount of a peptide or polypeptide may, preferably, comprises the steps of (a) contacting the peptide with a specific ligand, (b) (optionally) removing non-bound ligand, (c) measuring the amount of bound ligand, i.e. the complex of the ligand formed in step(a). According to a preferred embodiment, said steps of contacting, removing and measuring may be performed by an analyzer unit of the system disclosed herein. According to some embodiments, said steps may be performed by a single analyzer unit of said system or by more than one analyzer unit in operable communication with each other. For example, according to a specific embodiment, said system disclosed herein may include a first analyzer unit for performing said steps of contacting and removing and a second analyzer unit, operably connected to said first analyzer unit by a transport unit (for example, a robotic arm), which performs said step of measuring.

The bound ligand, i.e. the ligand or the ligand/peptide complex, will generate an intensity signal. Binding according to the present invention includes both covalent and non-covalent binding. A ligand according to the present invention can be any compound, e.g., a peptide, polypeptide, nucleic acid, or small molecule, binding to the peptide or polypeptide described herein. Preferred ligands include antibodies, nucleic acids, peptides or polypep-tides such as receptors or binding partners for the peptide or polypeptide and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab)2 fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant ami-no acid residues of the donor antibody as well. Such hybrids can be prepared by several methods well known in the art. Preferably, the ligand or agent binds specifically to the pep-tide or polypeptide. Specific binding according to the present invention means that the lig-and or agent should not bind substantially to ("cross-react" with) another peptide, poly-pep-tide or substance present in the sample to be analyzed. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. Preferably, said method is semi-quantitative or quantita-tive. Further suitable techniques for the determination of a polypeptide or peptide are de-scribed in the following.

Binding of a ligand may be measured directly, e.g. by NMR or surface plasmon resonance. Measurement of the binding of a ligand, according to preferred embodiments, is performed by an analyzer unit of a system disclosed herein. Thereafter, an amount of the measured binding may be calculated by a computing device of a system disclosed herein. If the ligand also serves as a substrate of an enzymatic activity of the pep-tide or polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for an detectable, preferably measurable, amount of product to be produced. Instead of measuring the amount of product, the time necessary for appearance of a given (e.g. detectable) amount of product can be measured. Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a pep-tide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluo-rescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, avail-able as ready-made stock solution from Roche Diagnostics), CDP-Star™ (Amersham Bio-sciences), ECF™ (Amersham Biosciences). A suitable enzyme-substrate combination may result in a colored reaction product, fluorescence or chemoluminescence, which can be measured according to methods known in the art (e.g. using a light-sensitive film or a suit-able camera system). As for measuring the enyzmatic reaction, the criteria given above apply analogously. Typical fluorescent labels include fluorescent proteins (such as GFP and its derivatives), Cy3, Cy5, Texas Red, Fluoresce-in, and the Alexa dyes (e.g. Alexa 568). Further fluorescent labels are available e.g. from Molecular Probes (Oregon). Also the use of quantum dots as fluorescent labels is contemplated.

Typical radioactive labels include 35S, 125I, 32P, 33P and the like. A radioactive label can be detected by any method known and appropriate, e.g. a light-sensitive film or a phosphor imager. Suitable meas-urement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labeling or other detec-tion methods as described above.

The amount of a peptide or polypeptide may be, also preferably, determined as follows: (a) contacting a solid support comprising a ligand for the peptide or polypeptide as specified above with a sample comprising the peptide or polypeptide and (b) measuring the amount peptide or polypeptide which is bound to the support. The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available col-umn materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan 2002, Trends Biotechnol. 20(1):9-12). In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744,305).

Preferably, the amount of the markers as referred to herein are determined by using the assays described in Example 1 and 2.

The term "amount" as used herein encompasses the absolute amount of a polypeptide or peptide, the relative amount or concentration of the said polypeptide or peptide as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response amounts determined from biological read out systems in response to the peptides or intensity signals obtained from specifically bound ligands. It is to be understood that values correlating to the aforementioned amounts or parameters can also be obtained by all standard mathematical operations.

The term "comparing" as used herein encompasses comparing the amount of a marker as referred to herein, in particular of peptide or polypeptide comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in step (b) of the method of the present invention may be carried out manually or by a computing device (e.g., of a system disclosed herein). For a computer assisted comparison, the value of the determined amount may be compared to values corresponding to suitable references which are stored in a database by a computer program. The computer program may further evaluate the result of the comparison, i.e. automatically provides the desired assessment in a suitable output format. The said result may, preferably, serve as an aid in assessing whether the subject shall be subjected to an imaging based diagnostic assessment as set forth herein elsewhere, or not. For example, a result of a comparison may be given as raw data (absolute or relative amounts), and in some cases as an indicator in the form of a word, phrase, symbol, or numerical value which may be indicative of a particular diagnosis/assessment. Therefore, the reference amount is to be chosen so that either a difference or a similarity in the compared amounts allows for carrying out the assessment or diagnosis as disclosed herein.

The term "reference amount" as used herein refers to an amount which allows for allocation of a subject into either the group of subjects who shall be subjected to an imaging based diagnostic assessment, or into a group of subjects who shall not be subjected to an imaging based diagnostic assessment. Such a reference amount can be a threshold amount which separates these groups from each other. Accordingly, the reference amount for a biomarker as referred to herein, in particular of a cardiac Troponin or FGF-23, shall be an amount which allows for allocation of a subject into a group of subjects who shall be subjected to an imaging based diagnostic assessment, or into a group of subjects who shall not be subjected to an imaging based diagnostic assessment. A suitable threshold amount separating the two groups can be calculated without further ado by the statistical tests referred to herein elsewhere based on amounts of the marker as referred to herein from either a subject or group of subjects who shall be subjected to the assessment, or a subject or group of subjects who shall not be subjected to the assessment. Preferred reference amounts which can be derived from the aforementioned subjects or group of subjects are indicated elsewhere herein.

The reference amount may be used to define and establish a threshold amount. The threshold amount, preferably, allows for a rule-in and/or a rule-out that the subject shall be subjected to an imaging based diagnostic assessment. Said rule-in and/or rule-out may be provided by the computing device of a system disclosed herein based on said comparison of the calculated "amount" to a reference or a threshold. For example, a computing device of a system may provide an indicator, in the form of a word, symbol, or numerical value which is indicative of a rule-in or rule-out. The reference amount applicable for an individual subject may vary depending on various physiological parameters such as age, gender, or subpopulation, as well as on the means used for the determination of the polypeptide or peptide referred to herein. A suitable reference amount may be determined from a reference sample to be analyzed together, i.e. simultaneously or subsequently, with the test sample.

Preferably, the reference amount is a calculated reference amount. Preferably, the calculated reference amount shall allow for differentiating between a subject who shall be subjected to an imaging based diagnostic assessment, and subject who shall not be subjected to an imaging based diagnostic assessment. Reference amounts can, in principle, be calculated for a cohort of subjects as specified above based on the average or mean values for a given biomarker by applying standard statistically methods. In particular, accuracy of a test such as a method aiming to diagnose an event, or not, is best described by its receiver-operating characteristics (ROC) (see especially Zweig 1993, Clin. Chem. 39:561-577). The ROC graph is a plot of all of the sensitivity/specificity pairs resulting from continuously varying the decision threshold over the entire range of data observed. The clinical performance of a diagnostic method depends on its accuracy, i.e. its ability to correctly allocate subjects to a certain assessment, prognosis or diagnosis. The ROC plot indicates the overlap between the two distributions by plotting the sensitivity versus 1-specificity for the complete range of thresholds suitable for making a distinction. On the y-axis is sensitivity, or the true-positive fraction, which is defined as the ratio of number of true-positive test results to the product of number of true-positive and number of false-negative test results. This has also been referred to as positivity in the presence of a disease or condition. It is calculated solely from the affected subgroup. On the x-axis is the false-positive fraction, or 1-specificity, which is defined as the ratio of number of false-positive results to the product of number of true-negative and number of false-positive results. It is an index of specificity and is calculated entirely from the unaffected subgroup. Because the true- and false-positive fractions are calculated entirely separately, by using the test results from two different subgroups, the ROC plot is independent of the prevalence of the event in the cohort. Each point on the ROC plot represents a sensitivity/-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. If the ROC plot falls completely below the 45° diagonal, this is easily remedied by reversing the criterion for "positivity" from "greater than" to "less than" or vice versa. Qualitatively, the closer the plot is to the upper left corner, the higher the overall accuracy of the test. Dependent on a desired confidence interval, a threshold can be derived from the ROC curve allowing for the diagnosis or prediction for a given event with a proper balance of sensitivity and specificity, respectively. Accordingly, the reference to be used for the aforementioned method of the present invention can be, preferably, a threshold or cut off amount and can be generated, preferably, by establishing a ROC for said cohort as described above and deriving a threshold amount therefrom. Dependent on a desired sensitivity and specificity for a diagnostic method, the ROC plot allows deriving suitable thresholds.

A preferred reference amount is within a range from 5 to 6 pg/ml for a cardiac Troponin, in particular for Troponin T. A particularly preferred reference amount is 5.9 pg/ml.

A preferred reference amount is within a range from 73 to 77 pg/ml for FGF-23. A particularly preferred reference amount is 74 RU/ml. Preferably, the amount of the markers are determined by using the assays is described in Examples 1 and 2.

Preferably, the following applies as diagnostic algorithm (in particular if the reference is a calculated reference amount):

Preferably, an increased amount of the marker (and, thus, of a cardiac troponin and/or FGF-23) in the sample from the subject as compared to the reference amount indicates that the subject shall be subjected to imaging based diagnostic assessment. Also preferably, a decreased amount of the marker(s) in the sample from the subject as compared to the reference amount indicates that the subject shall not be subjected to imaging based diagnostic assessment.

As set forth herein above, the reference amount can be derived from a subject or group of subjects which is (are) known to be susceptible to an imaging based diagnostic assessment. In this case, an amount of the marker(s) to be determined in the context of the present invention which is (are) essentially identical or which is (are) larger than the reference amount(s) indicates that the subject to be tested shall be subjected to an imaging based diagnostic assessment. Preferably, the reference amount is derived from a sample of said subject or from samples of said group or subjects. Preferably, a subject who is known to be susceptible to an imaging based diagnostic assessment is a subject who suffers from abnormal midwall fractioning (the term "abnormal midwall fractioning" is specified elsewhere herein).

Preferably, by applying the aforementioned reference amount it can be ruled in that the subject shall be subjected to an imaging based assessment.

Additionally or alternatively, the reference amount can be, preferably, derived from a subject or group of subjects which is (are) known not to be susceptible to an imaging based diagnostic assessment. In this case, an amount of the marker (s) to be determined in the context of the present invention which is (are) essentially identical or which is (are) lower than the reference amount(s) indicates that the subject to be tested shall not be subjected to an imaging based diagnostic assessment. Preferably, the reference amount is derived from a sample of said subject or from samples of said group or subjects. Preferably, a subject who is known not to be susceptible to an imaging based diagnostic assessment is a subject who does not suffer from abnormal midwall fractioning (the term "abnormal midwall fractioning" is specified elsewhere herein).

Preferably, by applying the aforementioned reference amount it can be ruled out that the subject shall be subjected to an imaging based assessment.

Further, if the reference amount is derived from a subject or group of subjects which is (are) known not to be susceptible to an imaging based diagnostic assessment, in particular from a subject or group of subjects who does/do not suffer from abnormal midwall fractioning, the following applies as diagnostic algorithm: Preferably, an amount of a cardiac Troponin, in particular, of Troponin T, that is at least 10%, or, more preferably, at least 25% larger than the reference amount of the cardiac Troponin, in particular of Troponin T, is indicative for a subject who shall be subjected to an imaging based diagnostic assessment. Also preferably, an amount of FGF-23, that is at least 5%, or, more preferably, at least 10% larger, or, even more preferably at least 25% larger than the reference amount of FGF-23 is indicative for a subject who shall be subjected to an imaging based diagnostic assessment.

The definition of the term "subject" is given elsewhere herein. The definitions also apply to the reference subject(s) in accordance with the methods of the present invention (i.e. to the subjects from which the reference amounts are derived). Preferably, the subject to be tested and the reference subject(s) have the same age, gender and/or race. Accordingly, it is preferred that the reference amount is adjusted for age, gender and/or race. Also preferably, the subject to be tested and the reference subject(s) may suffer from hypertension, in particular, hypertension accompanied by the same risk factors (for risk factors, see elsewhere herein).

The markers as referred to herein can be determined alone. However, they may be determined together, i.e. the method of the present invention may encompass the determination of a cardiac Troponin and FGF-23.

Moreover, in an embodiment of the present invention it is contemplated to further determine the amount of vitamin D in step a) in addition to the determination of FGF-23, to calculate a ratio between the amount of FGF-23 and the amount of vitamin D in a further step a1), and to compare the, thus, calculated ratio with a reference ratio.

Accordingly, the present invention also relates to a method for assessing whether a subject shall be subjected to an imaging based diagnostic assessment comprising the steps of a) determining the amount of the Fibroblast Growth Factor 23 (FGF-23) and the amount of vitamin D in a sample from the subject,
   a1) calculating a ratio between the amount of FGF-23 and the amount of vitamin D, and
b) comparing the, thus, calculated ratio to a reference ratio, whereby it is assessed whether the subject shall be subjected to the imaging based diagnostic assessment.

The amounts of FGF-23 and vitamin D may be determined in different samples from the subject. However, it is also contemplated to determine the amounts in the same sample.

Preferably, the aforementioned method may further comprise the determination of the amount of a cardiac Troponin in the sample (in step a)), and, the comparison of the, thus, determined amount to a reference amount (in step b)).

Preferably, the assessment whether the subject shall be subjected to the imaging based diagnostic assessment is based on the results of the comparison(s) carried out in step b).

The ratio between the amount of FGF-23 and the amount of vitamin D may be the ratio of the amount of FGF-23 to the amount of vitamin D or it may be the ratio of the amount of vitamin D to the amount of FGF-23.

Suitable reference ratios can be determined by the skilled person without further ado as set forth herein above in the context of the reference amount.

Preferably, if the ratio is the ratio of the amount of FGF-23 to the amount of vitamin D, the following also applies as diagnostic algorithm:

Preferably, an increased ratio of the amount of FGF-23 to the amount of vitamin D in the sample from the subject as compared to the reference ratio (of the of the amount of FGF-23 to the amount of vitamin D) indicates that the subject shall be subjected to imaging based diagnostic assessment. Also preferably, a decreased ratio of the amount of FGF-23 to the amount of vitamin D in the sample from the subject as compared to the reference ratio (of the of the amount of FGF-23 to the amount of vitamin D) indicates that the subject shall not be subjected to imaging based diagnostic assessment.

The reference ratio of FGF-23 to vitamin D can be derived from a subject or group of subjects known to be susceptible to an imaging based diagnostic assessment. In this case, a ratio of FGF-23 to vitamin D which is essentially identical or which is larger than the reference ratio indicates that the subject shall be subjected to said assessment. Preferably, the reference ratio is derived from a sample of said subject or from samples of said group or subjects. Preferably, a subject known to be susceptible to an imaging based diagnostic assessment is a subject who suffers from abnormal MFS.

Preferably, by applying the aforementioned reference ratio it can be ruled in that the subject shall be subjected to said assessment.

Additionally or alternatively, the reference ratio of FGF-23 to vitamin D can be, preferably, derived from a subject or group of subjects known not to be susceptible to an imaging based diagnostic assessment. In this case, a ratio FGF-23 to vitamin D in the test sample which essentially identical or which is lower than the reference ratio indicates that the subject shall not be subjected to said assessment. Preferably, the reference ratio is derived from a sample of said subject or from samples of said group or subjects. Preferably, a subject known not to be susceptible to an imaging based diagnostic assessment is a subject who does not suffer from abnormal MFS.

Preferably, by applying the aforementioned reference ratio it can be ruled out that the subject shall be subjected to said assessment.

Also preferably, if the reference ratio of FGF-23 to vitamin D is derived from a subject or from a group of subjects known not to suffer from abnormal midwall fractioning, the following also applies as diagnostic algorithm: Preferably, an ratio of FGF-23 to vitamin D in the test sample that is at least 5%, or, more preferably, at least 10% larger than the reference ratio is indicative for a subject who shall be subjected to an imaging based diagnostic assessment.

The term "vitamin D" is well understood by the skilled person. As used herein, the term, preferably, relates to a group of fat-soluble prohormones, the two major forms of which are vitamin D2 (also referred to aw ergocalciferol) and vitamin D3 (also referred to a cholecalciferol). Preferably, the term encompasses vitamin D in any of its forms, in particular vitamin D1, vitamin D2, vitamin D3 or vitamin D4. Further, it is envisaged that the term encompasses any precursor thereof. Vitamin D is typically obtained in an organism from sun exposure, food, and supplements, is biologically inert and undergoes two hydroxylation reactions to be activated in the organism. For example, an active form of vitamin D found in humans is calcitriol.

It is known in the art that the most accurate method to determine the amount of vitamin D is via the determination of 25-hydroxyvitamin D. 25-hydroxyvitamin D is a prehormone that is produced in the liver by hydroxylation of vitamin D3 (cholecalciferol) by the enzyme cholecalciferol 25-hydroxylase. Therefore, the term "vitamin D", in particular, refers to 25-hydroxyvitamin D. Accordingly, it is particularly preferred in the context of the present invention, to determine the amount of 25-hydroxyvitamin D in a sample from the subject.

In a preferred embodiment of the aforementioned method, the reference amount (ratio) of the marker(s) to be determined in the context of the method, is the amount (ratio) of the marker(s) in a sample from the (test) subject that has been obtained prior to the sample as set forth in step a).

In the context of the present application, the sample that has been obtained prior to the sample as set forth in step a), is also referred as "first sample", wherein the test sample set forth in step a), is referred to a "second sample" since it shall be obtained after the first sample.

Accordingly, the present invention relates to a method whether a subject shall be subjected to an imaging based diagnostic assessment comprising the steps
  a) determining the amount(s) of a cardiac Troponin and/or Fibroblast Growth Factor 23 (FGF-23) in a first sample and a second sample from the subject, and
  b) comparing the, thus, determined amount(s) in the second sample to the amount(s) in the first sample, whereby it is assessed whether the subject shall be subjected to an imaging based diagnostic assessment.

As set forth herein above, the second sample shall have been obtained after the first sample (in other words: the first sample shall have been obtained prior to the second sample). It is particularly contemplated that the second sample is obtained after a reasonable period of time after obtaining the first sample. It is to be understood, that the amounts of biomarkers referred herein, do not instantly change (e.g. within 1 minute or 1 hour). Therefore, "reasonable" in this context refers to intervals between obtaining the first and second sample which intervals allow the biomarker(s) to adjust. Preferably, the second sample shall have been obtained 1 to 24 months after the first sample. More preferably, the second sample shall have been obtained 6 to 18 months after the first sample. Even more preferably, the second sample shall have been obtained 6 to 12 months after the first sample. Most preferably, the second sample shall have been obtained 9 to 12 months after the first sample. According the first sample shall have been obtained, preferably, 1 to 24 months, more preferably, 6 to 18 months, even more preferably, 6 to 12 months, or, most preferably, 9 to 12 months prior to the second sample.

It is also envisaged to assess the time course of the amount of the markers as referred to in the method of the present invention, i.e. of a cardiac Troponin and/or of FGF-23 (or the time course of a ratio between FGF-23 and vitamin D in a subject as set forth herein. Accordingly, the aforementioned method may comprise the additional step of determining the amount of a cardiac Troponin and/or FGF-23 (or a ratio between FGF-23 and vitamin D) in at least one further sample from said subject (thus, in a third sample, in a fourth sample, in a fifth sample etc.) and comparing the, thus, determined amount (ratio) with the amount of said cardiac Troponin and FGF-23 ratio (or ratio between FGF-23 and vitamin D), respectively, in said first sample and/or said second sample and/or any sample that was obtained before said at least one further sample was obtained. For preferred time intervals for obtaining the samples, please see above.

Preferably, an increase and, more preferably, a significant increase, and, most preferably, a statistically significant increase of the amount of a cardiac Troponin and/or FGF-23 (and/or of the ratio of the amount of FGF-23 to the amount of vitamin D) in the second sample as compared the first sample indicates that the subject shall be subjected an imaging based diagnostic assessment. Preferably, a decrease and, more preferably, a significant decrease, and, most preferably, a statistically significant decrease of the amount of a cardiac Troponin and/or FGF-23 (and/or of the ratio of the amount of FGF-23 to the amount of vitamin D), or an essentially unchanged amount of a cardiac Troponin and/or FGF-23 (or an essentially unchanged ratio) in the second sample as compared to the first sample indicates that the subject shall not be subjected to an imaging based diagnostic assessment.

Particularly, a significant increase is an increase of a size which is considered to be significant for the assessment, particularly said increase is considered statistically significant.

The terms "significant" and "statistically significant" are known by the person skilled in the art. Thus, whether an increase or decrease is significant or statistically significant can be determined without further ado by the person skilled in the art using various well known statistic evaluation tools.

Preferred significant increases of the amount of a cardiac Troponin and/or of FGF-23 (or a ratio of FGF-23 to vitamin D), preferably of the amount (ratio) of the biomarker(s) in a blood, serum or plasma sample, which have been found in the course of the invention to be indicative for subject who shall be subjected to an imaging based diagnostic assessment, or not, given herein below.

If the marker is a cardiac Troponin, the following applies:

Preferably, an amount of a cardiac Troponin, in particular, of Troponin T, in the second sample that is at least 10%, or, more preferably, at least 25% larger than the reference amount (the amount of the cardiac Troponin in the first sample) is indicative for a subject who shall be subjected to an imaging based diagnostic assessment.

Further, according to the invention, an increase of the amount of a cardiac Troponin, in particular of Troponin T, in the second sample compared to the amount in the first sample, preferably, of at least 0.5 pg/ml, more preferably of at least 1.0 pg/ml and even, more preferably, of at least 1.5 pg/ml, of at least 2.0 pg/ml, or of at least 2.5 pg/ml, of at least 3.0 pg/ml and most preferably of at least 4.0 pg/ml is considered to be significant and, thus, indicates that the subject shall be subjected to an imaging based diagnostic assessment.

If the marker is FGF-23, the following applies:

Preferably, an amount of a FGF-23, in the second sample that is at least 5%, or, more preferably, at least 10% larger than the reference amount (the amount of FGF-23 in the first sample) is indicative for a subject who shall be subjected to an imaging based diagnostic assessment.

Further, according to the invention, an increase of the amount of FGF-23 in the second sample compared to the amount in the first sample, preferably, of at least 1.0 pg/ml, more preferably of at least 2.0 pg/ml and even, more preferably, of at least 3.0 pg/ml, of at least 4.0 pg/ml, or of at least 5.0 pg/ml, of at least 6.0 pg/ml and most preferably of at least 7.0 pg/ml is considered to be significant and, thus, indicates that the subject shall be subjected to an imaging based diagnostic assessment.

If the ratio of FGF-23 to vitamin D is determined, the following applies.

Preferably, a ratio, in the second sample that is at least 5%, or, more preferably, at least 10% larger than the reference ratio (the ratio in the first sample) is indicative for a subject who shall be subjected to an imaging based diagnostic assessment.

In a preferred embodiment of the aforementioned method, the subject to be tested does not suffer from abnormal MFS at the time at which the first sample was obtained. Further, it preferred that the subject does not suffer from diastolic and/or systolic dysfunction at the time at which the first sample was obtained. However, the subject shall suffer from hypertension at the time at which the first sample was obtained. The hypertension may be accompanied by risk factors as set forth herein elsewhere. Preferably, the is classified as stage A subject according to the ACC/AHA classification as referred to above at the time at which the first sample was obtained.

Method for Diagnosing Abnormal Midwall Fractional Shortening

The definitions and explanations given herein above apply mutatis mutandis to the following.

The present invention also relates to a method for diagnosing abnormal midwall fractional shortening (MFS) in a subject comprising the steps of a) determining the amount of a cardiac Troponin and/or Fibroblast Growth Factor 23 (FGF-23) in a sample from the subject, and b) comparing the, thus, determined amount(s) to a reference amount (reference amounts), whereby abnormal midwall fractional shortening is diagnosed.

Preferably, it is assessed whether the subject suffers from abnormal MFS by carrying out the further step of c) assessing whether the subject suffers from abnormal MFS, based on the results of the comparison carried out in step b).

The method of the present invention, preferably, is an ex vivo or in vitro method. Moreover, it may comprise steps in addition to those explicitly mentioned above. For example, further steps may relate to sample pre-treatments or evaluation of the results obtained by the method. The method may be carried out manually or assisted by automation. Preferably, step (a) and/or (b) may in total or in part be assisted by automation, e.g., by a suitable robotic and sensory equipment for the determination in step (a) or a computer-implemented comparison and/or differentiation based on said comparison in step (b).

The term "diagnosing" as used herein, preferably, means assessing whether a subject as referred to herein suffers from abnormal midwall fractional shortening (MFS), or not. The term abnormal midwall fractional shortening has been defined elsewhere herein.

As will be understood by those skilled in the art, such an assessment is usually not intended to be correct for 100% of the subjects to be diagnosed. The term, however, requires that the assessment is correct for a statistically significant portion of the subjects (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001.

The term "reference amount" has been defined elsewhere herein. In the context of the aforementioned method, the term refers to an amount which allows for allocation of a subject into either the group of subjects suffering from abnormal MFS or into a group of subjects not suffering from abnormal MFS (and, thus, having a normal MFS). Such a reference amount can be a threshold amount which separates these groups from each other. Accordingly, the reference amount for a biomarker as referred to herein, in particular of a cardiac Troponin or FGF-23, shall be an amount which allows for allocation of a subject into a group of subjects suffering from abnormal MFS, or into a group of subjects not suffering from abnormal MFS. A suitable threshold amount separating the two groups can be calculated without further ado by the statistical tests referred to herein elsewhere based on amounts of the marker as referred to herein from either a subject or group of subjects known to suffer from abnormal MFS, or a subject or group of subjects known not to suffer from abnormal MFS. Preferred reference amounts which can be derived from the aforementioned subjects or group of subjects are indicated elsewhere herein.

Preferably, the following applies as diagnostic algorithm:

Preferably, an increased amount of the biomarker (or increased amounts of the biomarker) in the sample from the subject as compared to the reference amount (or reference amounts) indicate(s) that the subject suffers from abnormal MFS, and wherein a decreased amount (or decreased amounts) in the sample from the subject as compared to the reference amount (or reference amounts) indicate(s) that the subject does not suffer from abnormal MFS. Preferably, a subject who does not suffer from abnormal MFS has a normal MFS.

As set forth herein above, the reference amount can be derived from a subject or group of subjects known to suffer from abnormal MFS. In this case, an amount (amounts) of the marker(s) to be determined in step a) which are essentially identical or which is (are) larger than the reference amount(s) indicate(s) that the subject to be tested suffers from abnormal MFS. Preferably, the reference amount is derived from a sample of said subject or from samples of said group or subjects.

Preferably, by applying the aforementioned reference amount abnormal MFS can be ruled in.

Additionally or alternatively, the reference amount can be, preferably, derived from a subject or group of subjects known not to suffer from abnormal MFS. In this case, an amount (amounts) of the marker(s) to be determined in step a) of the method of the present invention which is (are) essentially identical or which is (are) lower than the reference amount(s) indicate(s) that the subject does not suffer from abnormal MFS. Preferably, the reference amount is derived from a sample of said subject or from samples of said group or subjects.

Preferably, by applying the aforementioned reference amount abnormal MFS can be ruled out.

Preferably, if the reference amount(s) is (are) are derived from a subject or from a group of subjects known not to suffer from abnormal midwall fractioning, the following also may applies as diagnostic algorithm: Preferably, an amount of a cardiac Troponin, in particular, of Troponin T, that is at least 10%, or, more preferably, at least 25% larger than the reference amount of the cardiac Troponin, in particular of Troponin T, is indicative for a subject who suffers from abnormal MFS. Also preferably, an amount of FGF-23, that is at least 5%, or, more preferably, at least 10% larger than the reference amount of FGF-23 is indicative for a subject who suffers from abnormal MFS.

The definition of the term "subject" is given elsewhere herein. The definitions also apply to the reference subject(s). Preferably, the subject to be tested and the reference subject(s) have the about same age (+/− years, preferably the same age), the same gender and/or race. Also preferably, the subject to be tested and the reference subject(s) may suffer from hypertension, in particular, hypertension accompanied by the same risk factors (for risk factors, see elsewhere herein).

Moreover, in an embodiment of the present invention it is contemplated to further determine the amount of vitamin D in step a) in addition to the determination of FGF-23, to calculate a ratio between the amount of FGF-23 and the amount of vitamin D in a further step a1), and to compare the, thus, calculated ratio with a reference ratio.

Accordingly, the present invention also relates to a method for diagnosing abnormal midwall fractional shortening (MFS) in a subject, comprising the steps of
a) determining the amount of the Fibroblast Growth Factor 23 (FGF-23) and the amount of vitamin D in a sample from the subject,
   a1) calculating a ratio between the amount of FGF-23 and the amount of vitamin D, and
b) comparing the, thus, calculated ratio to a reference ratio, whereby it is abnormal midwall fractional shortening is diagnosed.

The amounts of FGF-23 and vitamin D may be determined in different samples from the subject. However, is particularly contemplated to the determined the amounts in the same sample.

Optionally, the method may further comprise the determination of the amount of a cardiac Troponin in the sample (in step a)), and, the comparison of the, thus, determined amount to a reference amount (in step b)).

Preferably, the assessment whether the subject shall be subjected to the imaging based diagnostic assessment is based on the results of the comparison(s) carried out in step b).

The ratio between the amount of FGF-23 and the amount of vitamin D may be the ratio of the amount of FGF-23 to the amount of vitamin D or it may be the ratio of the amount of vitamin D to the amount of FGF-23.

Suitable reference ratios can be determined by the skilled person without further ado as set forth herein above in the context of the reference amount.

Preferably, if the ratio is the ratio of the amount of FGF-23 to the amount of vitamin D, the following applies as diagnostic algorithm:

Preferably, an increased ratio of the amount of FGF-23 to the amount of vitamin D in the sample from the subject as compared to the reference ratio (of the of the amount of FGF-23 to the amount of vitamin D) indicates that the subject suffers from MFS. Also preferably, a decreased ratio of the amount of FGF-23 to the amount of vitamin D in the sample from the subject as compared to the reference ratio (of the of the amount of FGF-23 to the amount of vitamin D) indicates that the subject does not suffer from abnormal MFS.

Preferably, if the ratio of FGF-23 to vitamin D is determined, the following applies as well:

The reference ratio of FGF-23 to vitamin D can be derived from a subject or group of subjects known to suffer from abnormal MFS. In this case, a ratio of FGF-23 to vitamin D which is essentially identical or which is larger than the reference ratio indicates that the subject to be tested suffers from abnormal MFS. Preferably, the reference ratio is derived from a sample of said subject or from samples of said group or subjects.

Additionally or alternatively, the reference ratio of FGF-23 to vitamin D can be, preferably, derived from a subject or group of subjects known not to suffer from abnormal MFS. In this case, a ratio FGF-23 to vitamin D in the test sample which essentially identical or which is lower than the reference ratio indicates that the subject does not suffer from abnormal MFS. Preferably, the reference amount is derived from a sample of said subject or from samples of said group or subjects.

Preferably, if the reference ratio of FGF-23 to vitamin D is derived from a subject or from a group of subjects known not to suffer from abnormal midwall fractioning, the following also applies as diagnostic algorithm: Preferably, an ratio of FGF-23 to vitamin D in the test sample that is at least 5%, or, more preferably, at least 10% larger than the reference ratio is indicative for a subject who suffers from abnormal MFS.

A particularly, preferred reference ratio derived from a subject or from a group of subjects known not to suffer from abnormal midwall fractioning, is the median ratio in a group of such subjects. Preferably, the reference ratio is 5.3.

In a preferred embodiment, the method of the present invention further comprises the step of recommending a therapy, if the subject to be tested suffers from abnormal MFS and/or if the subject to be tested shall be subjected to an imaging based diagnostic assessment.

Preferred therapies as used in the context of the present invention encompass life style changes, diet regimen, interventions on the body as well as administration of appropriate drugs for the treatment of the subject.

Pharmaceuticals suitable for the treatment are well known in the art, see e.g. Heart Disease, 2008, 8th Edition, Eds. Braunwald, Elsevier Sounders, chapter 24 (in respect to heart failure) and chapter 41 (in respect to hypertension). These treatments are a part of the present invention.

Life style changes include smoking cessation, moderation of alcohol consumption, increased physical activity, weight loss, sodium (salt) restriction, weight management and healthy eating, daily fish oil, salt restriction.

The therapy may also include interventions. One preferred intervention in the context of the present invention is administration of antihypertensive medication with a preference for angiotensin-converting enzyme (ACE) inhibitors, Angiotensin-II-receptor blocker (ARB), aldosteron antagonists, beta blockers versus diuretics and Calcium antagonists.

Preferably, administration of one or more of the following drugs should be recommended:

Diuretics like loop diuretics, thiazide and thiazide-like diuretics, K-sparing diuretics, type I mineralocorticoid receptor antagonists, antialdosterone, carbonic anhydrase inhibitors, vasopres sure antagonists.

Beta blockers like proprenolol, metoprolol, bisoprolol, carvedilol, bucindolol, nebivolol; Calcium antagonists like dihydropyridines, verapamil, diltiazem;

Adrenergic agonists, like dobutamine, dopamine, epinephrine, isoprotenerol, norepinephrine, phenylephrine;

Positive inotropic agents, like digoxin, digitoxin;

ACE inhibitors like Enalapril, Captopril, Ramipril, Trandolapril;

Angiotensin receptor antagonists like Losartan, Valsartan, Irbesartan, Candesartan, Telmisartan, Eprosartan;

Adosterone antagonists like Eplerone, Spironolactone, Canrenone, Mexrenone, Prorenone; statines, in particular Atorvastatin, Fluvastatin, Lovastatin, Pravastatin, Rosuvastatin, Simvastatin;

Hydazaline and isosorbide dirritrate

Method for Predicting the Risk of Mortality and/or of a Cardiovascular Event

The present invention further relates to a method for predicting the risk of mortality and/or of a cardiovascular event in a subject comprising the steps of,
  a) determining, in a sample from said subject, the amount of IGFBP7 and/or the amount of FGF-23, and
  b) comparing the amount (or the amounts) as determined in step a) to a reference amount (or to reference amounts), whereby the risk of mortality and/or a cardiovascular event in said subject is predicted.

In an embodiment of the aforementioned method, it is contemplated to further determine the amount of vitamin D in step a) in addition to the determination of FGF-23, to calculate a ratio between the amount of FGF-23 and the amount of vitamin D, and to compare the, thus, calculated ratio with a reference ratio.

Accordingly, the present invention also encompasses a method for predicting the risk of mortality and/or a cardiovascular event in a subject comprising the steps of
  a) determining the amount of the Fibroblast Growth Factor 23 (FGF-23) and the amount of vitamin D in a sample from the subject,
    a1) calculating a ratio between the amount of FGF-23 and the amount of vitamin D, and
  b) comparing the, thus, calculated ratio to a reference ratio, whereby the risk of mortality and/or a cardiovascular event in said subject is predicted.

Of course, also the amount of IGFBP7 may be determined in addition to the amounts of FGF-23 and vitamin D:

Accordingly, the present invention also encompasses a method for predicting the risk of mortality and/or a cardiovascular event in a subject comprising the steps of
  a) determining the amounts of IGFBP7, Fibroblast Growth Factor 23 (FGF-23) and vitamin D in a sample from the subject,
    a1) calculating a ratio between the amount of FGF-23 and the amount of vitamin D,
  b) comparing the, thus, calculated ratio to a reference ratio, and
    b1) comparing the amount of IGFBP7 to a reference ratio, whereby the risk of mortality and/or a cardiovascular event in said subject is predicted.

The ratio between the amount of FGF-23 and the amount of vitamin D may be the ratio of the amount of FGF-23 to the amount of vitamin D or it may be the ratio of the amount of vitamin D to the amount of FGF-23.

Preferably, the risk of mortality and/or of a cardiovascular event is predicted by carrying out the further step of c) predicting the risk of mortality and/or a cardiovascular event, based on the results of the comparison carried out in step b) (or in steps b) and ill).

The amounts of the biomarkers may be determined in different samples from the subject. However, it is also contemplated to determine the amounts in the same sample.

In a preferred embodiment, the method for predicting the risk of mortality and/or of a cardiovascular event further comprises the step of determining the amount of a brain natriuretic peptide, in particular of BNP or NT-proBNP, and/or the amount of a cardiac Troponin, in particular of Troponin T or I, in the sample from the subject, and the step of comparing the amount of said brain natriuretic peptide and/or the amount of the cardiac Troponin to a reference amount (or reference amounts).

The method of the present invention, preferably, is an ex vivo or in vitro method. Moreover, it may comprise steps in addition to those explicitly mentioned above. For example, further steps may relate to sample pre-treatments or evaluation of the results obtained by the method. The method of the present invention may be also used for monitoring, confirmation, and subclassification. The method may be carried out manually and/or assisted by automation. Preferably, step (a), (b), and/or (c) may in total or in part be assisted by automation, e.g., by a suitable robotic and sensory equipment for the determination in step (a) or a computer-implemented comparison in step (b).

The term "predicting" used herein refers to assessing the probability according to which a subject will die (e.g.

mortality caused by the heart failure) and/or develop a cardiovascular event, preferably an acute cardiovascular event such as an acute coronary syndrome (ACS) within a defined time window (predictive window) in the future. The predictive window is an interval in which the subject will develop a cardiovascular event or will die according to the predicted probability. The predictive window may be the entire remaining lifespan of the subject upon analysis by the method of the present invention. Preferably, however, the predictive window is an interval of one, two, three, four, five, ten, fifteen or 20 years after the method of the present invention has been carried out (more preferably and precisely, after the sample to be analyzed by the method of the present invention has been obtained). Most preferably, said predictive window is an interval of four or five years. As will be understood by those skilled in the art, such an assessment is usually not intended to be correct for 100% of the subjects to be analyzed. The term, however, requires that the assessment will be valid for a statistically significant portion of the subjects to be analyzed. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the prediction will be correct for at least 60%, at least 70%, at least 80%, or at least 90% of the subjects of a given cohort.

The term "mortality" as used herein, preferably, relates to mortality from any cause, and, more preferably, from a cardiovascular event. The term "cardiovascular event" as used herein refers to any disorder of the cardiovascular system including preferably any acute cardiovascular event. Acute cardiovascular events are, preferably, stable angina pectoris (SAP) or acute coronary syndrome (ACS). ACS patients can show unstable angina pectoris (UAP) or myocardial infarction (MI). MI can be an ST-elevation MI (STEMI) or a non-ST-elevation MI (NSTEMI). NSTE-ACS as used herein encompasses UAP and NSTEMI. The occurring of an MI can be followed by a left ventricular dysfunction (LVD), development of heart failure or even mortality. Further preferred cardiovascular events encompass cardiac brady- or tachyarrhythmias including sudden cardiac death and stroke (cerebrovascular events or accidents). Also, mortality can also refer to the death rate or the ratio of number of deaths to a given population of subjects.

The expression "predicting the risk of mortality and/or of a cardiovascular event" as used herein means that it the subject to be analyzed by the method of the present invention is allocated either into the group of subjects of a population having an elevated risk, or into a group having a reduced risk. An elevated risk as referred to in accordance with the present invention, preferably, means that the risk of developing a cardiovascular event or the risk of mortality within a predetermined predictive window is elevated significantly (i.e. increased significantly) for a subject with respect to the average risk for a cardiovascular event or cardiac mortality in a population of subjects. A reduced risk as referred to in accordance with the present invention, preferably, means that the risk of developing a cardiovascular event or the risk of mortality within a predetermined predictive window is reduced significantly for a subject with respect to the average risk for a cardiovascular event or cardiac mortality in a population of subjects. Particularly, a significant increase or reduction of a risk is an increase or reduction or a risk of a size which is considered to be significant for prognosis, particularly said increase or reduction is considered statistically significant. The terms "significant" and "statistically significant" are known by the person skilled in the art. Thus, whether an increase or reduction of a risk is significant or statistically significant can be determined without further ado by the person skilled in the art using various well known statistic evaluation tools.

Preferably, for a predictive window of four (or five) years, an elevated risk of mortality (or of a cardiovascular event) is within the range of 8.0% and 19.0%, more preferably within the range of 12.0% to 17.0%, most preferably, within the range of 8.0% to 16.0%. An elevated, and, thus increased risk of mortality as used herein, preferably, relates to a risk of more than 8.0%, preferably, more than 12.0%, more preferably, more than 17%, even more preferably, more than 20%, preferably, with respect to a predictive window of four (or 5 years). A reduced risk of mortality (or of a cardiovascular event) as used herein, preferably, relates to a risk of less than 8.0%, preferably, less than 6%, even more preferably, less than 4%, and is, most preferably within the range of 3.0% and 8.0%, preferably with respect to a predictive window of four years.

The term "subject" has been defined above. The definition of the term "subject" also applies to the aforementioned method. Thus, as set forth herein above in connection with the method for assessing whether a subject shall be subjected to an imaging based diagnostic assessment, the subject, e.g. shall have a normal ventricular mass.

The subject in the context of the aforementioned method of the present invention of predicting the risk of mortality and/or the risk of a cardiovascular event, preferably, does not suffer from heart failure and/or does not show overt symptoms of heart failure (see explanations above). Accordingly, the subject shall not suffer from heart failure classified as stage C or D according to the ACC/AHA classification (see reference above). Moreover, as set forth herein below, the patient does not have reduced left ventricular ejection fraction.

In a preferred embodiment of the aforementioned method, the subject, preferably, suffers from heart failure classified as stage A or stage B according to the ACC/AHA classification. In another preferred embodiment of the aforementioned method, the subject is healthy with respect to cardiac diseases and disorders. A subject who is healthy with respect to cardiac diseases and disorders is considered as a subject who does not suffer from cardiac diseases and disorders.

Preferably, the subject in the context of the aforementioned method does not suffer from systolic heart failure (in particular from systolic heart failure with reduced ejection fraction) and/or systolic dysfunction. Preferably, the subject shall have a preserved left ventricular ejection fraction. Accordingly, the subject to be tested may have a left ventricular ejection fraction (LVEF) of, preferably, more than 55%, more preferably, more than 60% and, most preferably, more than 65%.

The Insulin like growth factor binding protein (IGFBP) system plays an important role in cell growth and differentiation. It comprises two ligands, IGF-I and IGF-II, two receptors, type 1 and type 2 IGF receptors, and as of 1995 six IGF-binding proteins (IGFBPs), IGFBP-1 to -6 (Jones, J. I., et al., Endocr. Rev. 16 (1995) 3-34). Recently the IGFBP family has been expanded to in-dude the IGFBP-related proteins (IGFBP-rPs), which have significant structural similarities with the IGFBPs (Hwa, V., et al., Endocr. Rev 20 (1999) 761-787). Thus, the IGFBP superfamily includes the six conventional IGFBPs, which have high affinity for IGFs, and at least 10 IGFBP-rPs, which not only share the conserved amino-terminal domain of the IGFBPs but also show some degree of affinity for IGFs and insulin. The IGFBP-rPs are a group of cysteine-rich proteins that control diverse cellular functions, such as cellular growth, cell adhesion and migration, and synthesis of the extracellular matrix. In addition, these proteins might be involved in biological processes like tissue proliferation and differentiation, reproduction, angiogenesis, wound repair, inflammation, fibrosis, and tumorigenesis (Hwa, V., et al., Endocr. Rev 20 (1999) 761-787).

IGF binding protein 7 (=IGFBP7) is a 30-kDa modular glycoprotein known to be secreted by endothelial cells, vascular smooth muscle cells, fibroblasts, and epithelial cells (Ono, Y., et al., Biochem Biophys Res Comm 202 (1994) 1490-1496). In the literature this molecule has also been denominated as FSTL2; IBP 7; IGF binding protein related protein I; IGFBP 7; IGFBP 7v; IGFBP rPl; IGFBP7; IGFB-PRP1; insulin like growth factor binding protein 7; insulin like growth factor binding protein 7 precursor; MAC25; MAC25 protein; PGI2 stimulating factor; and PSF or Prostacyclin stimulating factor. Northern blot studies revealed a wide expression of this gene in human tissues, including heart, brain, placenta, liver, skeletal muscle, and pancreas (Oh, Y., et al., J. Biol. Chem. 271 (1996) 30322-30325).

IGFBP7 was initially identified as a gene differentially expressed in normal leptomeningeal and mammary epithelial cells, compared with their counterpart tumor cells, and named meningioma-associated cDNA (MAC25) (Burger, A. M., et al., Oncogene 16 (1998) 2459-2467). The expressed protein was independently purified as a tumor derived adhesion factor (later renamed angiomodulin) (Sprenger, C. C., et al., Cancer Res 59 (1999) 2370-2375) and as a prostacyclin stimulating factor (Akaogi, K., et al., Proc Natl Acad Sci USA 93 (1996) 8384-8389). It has additionally been reported as T1A12, a gene down-regulated in breast carcinomas (StCroix, B., et al., Science 289 (2000) 1197-1202).

Preferably, the term "IGFBP7" refers to human IGFBP7. The sequence of the protein is well known in the art and is e.g. accessible via GenBank (NP_001240764.1). IGFBP7 as used herein, preferably, encompasses also variants of the specific IGFBP7 polypeptides. For an explanation of the term "variants", please see above.

As set forth above, the aforementioned method may further comprise the determination of a the amount of brain natriuretic peptide and/or of the amount of a cardiac Troponin in a sample from the subject. The term "cardiac troponin" has been described elsewhere herein. As used herein, the term "brain natriuretic peptides", preferably, refers to Brain Natriuretic Peptide (BNP)-type peptides and variants thereof having the same predictive potential. BNP-type peptides comprise pre-proBNP, proBNP, NT-proBNP, and BNP. The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP). Preferably, brain natriuretic peptides according to the present invention are NT-proBNP, BNP, and variants thereof. BNP is the active hormone and has a shorter half-life than its respective inactive counterpart NT-proBNP. BNP is metabolized in the blood, whereas NT-proBNP circulates in the blood as an intact molecule and as such is eliminated renally. The in-vivo half-life of NT-proBNP is 120 min longer than that of BNP, which is 20 min (Smith 2000, J Endocrinol. 167: 239-46). Preanalytics are more robust with NT-proBNP allowing easy transportation of the sample to a central laboratory (Mueller 2004, Clin Chem Lab Med 42: 942-4). Blood samples can be stored at room temperature for several days or may be mailed or shipped without recovery loss. In contrast, storage of BNP for 48 hours at room temperature or at 4° Celsius leads to a concentration loss of at least 20% (Mueller loc.cit.; Wu 2004, Clin Chem 50: 867-73). Therefore, depending on the time-course or properties of interest, either measurement of the active or the inactive forms of the natriuretic peptide can be advantageous. The most preferred natriuretic peptides according to the present invention are NT-proBNP or variants thereof. As briefly discussed above, the human NT-proBNP, as referred to in accordance with the present invention, is a polypeptide comprising, preferably, 76 amino acids in length corresponding to the N-terminal portion of the human NT-proBNP molecule. The structure of the human BNP and NT-proBNP has been described already in detail in the prior art, e.g., WO 02/089657, WO 02/083913 or Bonow loc. cit. Preferably, human NT-proBNP as used herein is human NT-proBNP as disclosed in EP 0 648 228 B1. These prior art documents are herewith incorporated by reference with respect to the specific sequences of NT-proBNP and variants thereof disclosed therein. The NT-proBNP referred to in accordance with the present invention further encompasses allelic and other variants of said specific sequence for human NT-proBNP discussed above. Specifically, envisaged are variant polypeptides which are on the amino acid level preferably, at least 50%, 60%, 70%, 80%, 85%, 90%, 92%, 95%, 97%, 98%, or 99% identical to human NT-proBNP, preferably over the entire length of human NT-proBNP. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the said polypeptides have NT-proBNP properties. NT-proBNP properties as referred to herein are immunological and/or biological properties. Preferably, the NT-proBNP variants have immunological properties (i.e. epitope composition) comparable to those of human NT-proBNP. Thus, the variants shall be recognizable by the aforementioned means or ligands used for determination of the amount of the natriuretic peptides. Biological and/or immunological NT-proBNP properties can be detected by the assay described in Karl et al. (Karl 1999, Scand J Clin Lab Invest 230:177-181), Yeo et al. (Yeo 2003, Clinica Chimica Acta 338:107-115). Variants also include posttranslationally modified peptides such as glycosylated peptides. Further, a variant in accordance with the present invention is also a peptide or polypeptide which has been modified after collection of the sample, for example by covalent or non-covalent attachment of a label, particularly a radioactive or fluorescent label, to the peptide.

The term "reference amount" has been defined above. In the context with the aforementioned method, the reference amount for a biomarker as referred to herein, in particular of FGF-23, IGFBP7, a cardiac Troponin, or a brain natriuretic peptide shall be an amount which allows for allocation of a subject into a group of subjects having an elevated risk of mortality and/or of a cardiovascular event, or into a group of subjects having a reduced risk of mortality and/or of a cardiovascular event. A suitable threshold amount separating the two groups can be calculated without further ado by the statistical tests referred to herein elsewhere based on amounts of the marker as referred to herein from either a subject or group of subjects known to have an elevated risk of mortality and/or of a cardiovascular event, or a subject or group of subjects known to have a reduced risk of mortality and/or of a cardiovascular event. Preferred reference amounts which can be derived from the aforementioned subjects or group of subjects are indicated elsewhere herein.

Preferably, the following applies as diagnostic algorithm:

Preferably, the reference amount is derived from a subject or group of subjects known to have an elevated risk of mortality and/or of a cardiovascular event. In this case, an amount of the marker FGF-23 and/or an amount of IGFBP7 which is (are) essentially identical or which is (are) larger than the reference amount(s) indicates that the subject to be tested is at elevated risk of mortality and/or of a cardiovascular event. The same applies for the markers which may be further determined in the context of present invention, i.e. to the cardiac troponin and the brain natriuretic peptide.

Additionally or alternatively, the reference amount can be derived from a subject or group of subjects known to have reduced risk of mortality and/or of a cardiovascular event. In this case, an amount of the marker FGF-23 and/or an amount of IGFBP7 which is (are) essentially identical or which is (are) lower than the reference amount(s) indicates that the subject to be tested is at reduced risk of mortality and/or of a cardiovascular event. The same applies for the markers that may be further determined in the context of present invention, i.e. to the cardiac troponin and the brain natriuretic peptide.

Moreover, it is envisaged that the reference amount is a calculated reference amount. Preferably, the calculated reference amount shall allow for differentiating between a subject who is at elevated risk of mortality and/or a cardiovascular event, and subject who is at reduced risk of mortality and/or a cardiovascular event. Preferably, an increased amount (increased amounts) of the marker(s) is (are) indicative for a subject who is at elevated risk of mortality and/or a cardiovascular event, whereas a decreased amount (decreased amounts) of the marker(s) is (are) indicative for a subject who is at reduced risk of mortality and/or a cardiovascular event As set forth above, the aforementioned method may comprise the combined determination of FGF-23 and vitamin D, and the calculation of a reference ratio. Suitable reference ratios can be determined by the skilled person without further ado as set forth herein above in the context of the reference amount.

A preferred reference ratio for the ratio of the amount to FGF-23 to the amount of vitamin D is within a range from 4 to 8.5, in particular from 6.5 to 8.5. Further reference ratios of the amount to FGF-23 to the amount of vitamin D are preferably, 6.5, more preferably 7.5, or most preferably 8.5.

A preferred reference amount is within a range from 100 to 115 ng/ml for IGFBP7. A particularly preferred reference amount is 115 ng/ml.

Preferably, if the ratio is the ratio of the amount of FGF-23 to the amount of vitamin D, the following also applies as diagnostic algorithm:

Preferably, an increased ratio of the amount of FGF-23 to the amount of vitamin D in the sample from the subject as compared to the reference ratio (of the of the amount of FGF-23 to the amount of vitamin D) indicates that the subject is at elevated risk of mortality and/or of a cardiovascular event. Also preferably, a decreased ratio of the amount of FGF-23 to the amount of vitamin D in the sample from the subject as compared to the reference ratio (of the of the amount of FGF-23 to the amount of vitamin D) indicates that the subject is at reduced risk of mortality and/or of a cardiovascular event.

Also preferably, the reference ratio of FGF-23 to vitamin D can be derived from a subject or group of subjects known to have an elevated risk of mortality and/or of a cardiovascular event. In this case, a ratio of FGF-23 to vitamin D which is essentially identical or which is larger than the reference ratio indicates that the subject has an elevated risk of mortality and/or of a cardiovascular event.

Additionally or alternatively, the reference ratio of FGF-23 to vitamin D can be, preferably, derived from a subject or group of subjects known to have a reduced risk of mortality and/or of a cardiovascular event. In this case, a ratio FGF-23 to vitamin D in the test sample which essentially identical or which is lower than the reference ratio indicates that the subject a reduced risk of mortality and/or of a cardiovascular event.

Method for Diagnosing an Early Stage of Left Ventricular Hypertrophy (LVH)

It has been shown in the studies underlying the present invention that the combined determination of endostatin and a BNP-type peptide (such as NT-proBNP and/or BNP), or the combined determination of endostatin and a cardiac Troponin allows for reliable identification of subjects being in an early stage of left ventricular hypertrophy. The combined determination of these markers results in an improved diagnosis since the determination of endostatin on the one hand and of a BNP-type peptide or a cardiac Troponin on the other hand allows for the identification of different subgroups of subjects being in an early stage of LVH. An increased amount of one of the markers, or an increased amount of two markers is indicative for an early stage of LVH. If only the amount of one marker would be determined, some patients being in an early stage of LVH would be missed.

The combined determination of the markers is, in particular, advantageous in subjects having a preserved left ejection fraction since it allows for the intermediate phenotype in the progression from hypertension to systolic or diastolic dysfunction before LVH becomes more pronounced.

Accordingly, the present invention present invention pertains to a method for diagnosing an early stage of left ventricular hypertrophy in a subject having a preserved left ventricular ejection fraction, said method comprising the steps of
  a) determining the amount of endostatin in a sample from the subject, and
  b) determining the amount of a BNP-type peptide and/or of a cardiac Troponin in a sample from the subject, and
  c) comparing the amounts as determined in step a) and b) to reference amounts, whereby an early stage of left ventricular hypertrophy is diagnosed.

Preferably, the early stage of left ventricular hypertrophy is diagnosed by carrying out the further step of d) diagnosing whether the subject is in an early stage of left ventricular hypertrophy, or not, based on the results of the comparison carried out in step c).

The amounts of the markers in step a) and b) may be determined in the same sample from the subject, or in different samples from the subject.

The term "diagnosing" as used herein, preferably, means assessing whether a subject as referred to herein in the context with the aforementioned method suffers from an early stage of LVH, or not. As will be understood by those skilled in the art, such an assessment is usually not intended to be correct for 100% of the subjects to be diagnosed. The term, however, requires that the assessment is correct for a statistically significant portion of the subjects (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001.

In the context of the method of the present invention, it shall be diagnosed whether a subject is in an early stage of left ventricular hypertrophy (LVH), or not. The term "early stage of left ventricular hypertrophy" as used herein preferably, relates to subtle structural changes of the myocardium which take place in the progression from hypertension to heart failure. Accordingly, by carrying out the steps of the aforementioned method, it is possible to diagnose an intermediate phenotype in the progression from hypertension to heart failure. Accordingly, the term "early stage of left ventricular hypertrophy" preferably encompasses the stage of LVH in which the mass of the left ventricle is slightly increased. Preferably, the mass of the left ventricle is slightly increased, if the subject has a LVMI as indicated herein below.

Preferably, if the subject is male, the term "early stage of LVH" encompasses the stage of LVH in which the left ventricular mass index (and, thus, the ratio of the left ventricular mass to body surface, abbreviated LVMI) is in a range between 116 $g/m^2$ to 149 $g/m^2$, more preferably, in a range between 116 $g/m^2$ to 135 $g/m^2$, even more preferably, in a range between 116 $g/m^2$ to 130 $g/m^2$, and most preferably, in a range between 116 $g/m^2$ to 125 $g/m^2$.

Preferably, if the subject is female, the term "early stage of LVH" encompasses the stage of LVH in which the left ventricular mass index (and, thus, the ratio of the left ventricular mass to body surface, abbreviated LVMI) is in a range between 96 $g/m^2$ to 125 $g/m^2$, more preferably, in a range between 96 $g/m^2$ to 120 $g/m^2$ or in a range between 96 $g/m^2$ to 115 $g/m^2$, and most preferably, in a range between 96 $g/m^2$ to 108 $g/m^2$.

Accordingly, by carrying out the method of the present invention, it can be diagnosed whether the subject to be tested has left ventricular mass index as set forth above, or not.

Preferably, the LVMI values given herein are based on the method for assessing LVH as disclosed by Lang et al. (Recommendations for chamber quantification. Eur J Echocardiogr 2006; 7:79-108).

If follows from the above, that the subject to be tested shall not suffer from a pronounced form of LVH. Preferably, if the subject is male, the LVMI is lower (and, thus, not larger) than 149 $g/m^2$, 135 $g/m^2$, 130 $g/m^2$, or 125 $g/m^2$. Preferably, if the subject is female, the LVMI is lower (and, thus, not larger) than 125 $g/m^2$, 120 $g/m^2$, 115 $g/m^2$, or 108 $g/m^2$.

The term "subject" in connection with the aforementioned method relates to animals, preferably mammals, and, more preferably, humans. In a preferred embodiment, the subject is male. In another preferred embodiment, the subject is female. Further, the subject may be older than 65 years.

The subject in the context of the aforementioned method of the present invention, preferably, does not suffer from heart failure and/or does not show overt symptoms of heart failure (see explanations above). Accordingly, the subject shall not suffer from heart failure classified as stage C or D according to the ACC/AHA classification.

As set forth above, a subject who does not show overt symptoms of heart failure, may suffer from heart failure stage A or B according to the ACC/AHA classification referred to above. In connection with the aforementioned method of the present invention, the subject, thus preferably suffers from heart failure classified as stage A or, more preferably, from heart failure stage B according to the ACC/AHA classification (see J. Am. Coll. Cardiol. 2001; 38; 2101-2113, updated in 2005, see J. Am. Coll. Cardiol. 2005; 46; e1-e82).

In another preferred embodiment of the aforementioned method, the subject is healthy with respect to cardiac diseases and disorders. A subject who is healthy with respect to cardiac diseases and disorders is considered as a subject who does not suffer from cardiac diseases and disorders.

The subject in the context of the aforementioned method shall have a preserved left ventricular ejection fraction (LVEF). Accordingly, the subject shall have a left ventricular ejection fraction (LVEF) of, preferably, more than 55%, more preferably, more than 60% and, most preferably, more than 65%. Accordingly, the subject, preferably, does not suffer from systolic heart failure or systolic dysfunction. A definition of the term "systolic heart failure" has been given above.

The present invention is, in particular, advantageous in subjects suffering from hypertension, since the combined determination of the markers endostatin and/or a cardiac Troponin allows for diagnosing subtle structural changes of the myocardium which take place in the progression from hypertension to heart failure. Therefore, the subject preferably suffers from hypertension, in particular arterial hypertension (for an explanation of this term, see elsewhere herein)

Moreover, it is envisaged that the subject does not suffer from ACS and/or from coronary artery disease. In addition, the subject shall not have impaired renal function. (for a definition of these terms, see above). Further, the subject shall not be pregnant. Also preferably, the subject is not an athlete.

The terms "sample", "determining", "amount", "comparing" and "reference amount" are defined above. The definitions also apply with respect to the aforementioned method.

Also, a definition of the terms "cardiac Troponin" and "BNP-type peptides" to be determined in the context of the method of the present invention can be found above as well. Preferred cardiac Troponins are Troponin T and Troponin I. Preferred BNP-type peptides are NT-proBNP and BNP.

The marker Endostatin is well known in the art. Endostatin was originally isolated from murine hemangioendothelioma as a 20 kDA proteolytic fragment of type XVIII collagen (O'Reilly, M. S. et al., Cell 88 (1997) 277-285). Collagens represent a family of extracellular matrix proteins with a characteristic triple-helical conformation forming supra-molecular aggregates that play a dominant role in maintaining tissue structural integrity. Excessive collagen deposition leads to fibrosis disrupting the normal functioning of surrounding tissues. Collagen XVIII is a member of the Multiplexin family of collagens with multiple interruptions in the central triple-helical domain and a unique non-triple-helical domain at the C-terminus mainly in basement membranes. The sequence of the short isoform of human type alpha 1-chain of collagen XVIII (SwissProt: P39060) is e.g. disclosed in WO2010/124821 which herewith is incorporated by reference with respect to its entire disclosure content.

Endostatin is released from the alpha 1 chain of collagen XVIII by action of various proteolytic enzymes (for details see Ortega, N. and Werb, Z., Journal of Cell Science 115 (2002) 4201-4214—the full disclosure of this paper is herewith incorporated by reference). Endostatin as used herein is represented by the collagen XVIII fragment spanning from amino acid position 1337 to amino acid position 1519 of collagen XVIII as disclosed in WO2010/124821. The hinge region at the C-terminus of the alpha chain of collagen XVIII contains several protease sensitive sites and a number of enzymes, including neutrophil elastase, cathepsins and matrix metalloproteinases are known to generate endostatin by cleaving the collagen chain in this region. These proteases do not exclusively release endostatin but also may release other, larger fragments that contain the endostatin sequence. As obvious to the skilled artisan such larger fragments will also be measured by an immunoassay for endostatin.

The term "reference amount" has been defined elsewhere herein. As set forth above, the reference amount may be a calculated reference amount. Preferably, the calculated reference amounts shall allow for differentiating between a subject who is in an early stage of LVH, and a subject is not in an early stage of LVH.

In principle the following may apply as diagnostic algorithm: Preferably, the test subject is in an early stage of LVH, if (i) an amount of one of the determined markers (e.g. of endostatin or a brain natriuretic peptide, or of endostatin or a cardiac Troponin) is larger than the reference amount, or if (ii) the amounts of both markers are larger than the reference amounts. Preferably, the test subject is not in an early stage of LVH, if the amounts of both markers are lower than the reference amounts.

Suitable reference amounts which allow for diagnosing whether a subject is in an early stage of LVH, or not, can be determined by the skilled person. The reference amount for a biomarker as referred to herein in connection with the aforementioned method shall be an amount which allows for allocation of a subject into a group of subjects being in an early stage of left ventricular hypertrophy, and/or into a group of subjects not being in early stage of LVH. A suitable threshold amount separating the two groups can be calculated without further ado by the statistical tests referred to herein elsewhere based on amounts of the marker as referred to herein from either a subject or group of subjects known to be in an early stage of LVH, or a subject or group of subjects known not to be in an early stage of LVH.

As set forth herein above, the reference amounts for the biomarkers can be derived from a subject or group of subjects known to be in an early stage of LVH. In this case, an amount of at least one of the determined markers which is essentially identical or which is larger than the reference amount indicates that the subject is in an early stage of LVH. Accordingly, an early stage of LVH can be diagnosed, if the amount of one marker is essentially identical or larger than the reference amount.

Additionally or alternatively, the reference amounts for the biomarkers can be derived from a subject or group of subjects known not to be in an early stage of LVH. In this case, amounts of all markers (i.e. if two markers are determined, of both markers) which are essentially identical and/or which are lower than the reference amounts indicate that the subject is not in an early stage of LVH. Accordingly, the subject is not in an early stage of LVH, if the amount of both markers are essentially identical and/or larger than the reference amounts.

A preferred reference amount is within a range from 180 to 200 ng/ml for endostatin. A particularly preferred reference amount is 190 ng/ml.

A preferred reference amount for NT-proBNP is within a range from 180 to 250 pg/ml. A particularly preferred reference amount is about 200 pg/ml.

A preferred reference amount for Troponin T is within a range from 5 to 10 pg/ml. Preferably, the reference amount is 8 pg/ml.

In an embodiment of the present invention, the method further comprises the step of recommending a therapy, if the subject to be tested is in an early stage of LVH. Preferred therapies are disclosed in the context of the method for diagnosing abnormal MFS.

In a preferred embodiment of the present invention, the method further comprises the determination of the amount of at least one further marker selected from the group consisting of mimecan, Growth Differentiation Factor 15 (GDF-15), FGF-23 and vitamin D in the sample from the subject, and the comparison of the, thus, determined amount (or amounts) of said at least one further marker with a reference amount (reference amounts) for said at least one further marker. If the amounts of FGF-23 and/or vitamin D are determined, the ratio of FGF-23 to vitamin D (or vice versa) may be calculated, and compared to a reference ratio. A preferred combination is a of a cardiac Troponin, endostatin and FGF-23:vitamin D.

Mimecan is a small proteoglycan with leucin-rich repeats and a precursor comprising 298 amino acids. Other names of mimecan are OGN, osteoglycin, OG, OIF, SLRR3A.

Mimecan is a member of the secreted small leucine rich proteoglycans (SLRP) family with structurally related core proteins. The common feature shared by all SLRPs is the tandem leucine-rich repeat (LRR) units in the C-terminal half of the core protein. In the N-terminal region, however, each class of SLRP has a unique domain containing a cysteine cluster with conserved spacing called the LRR N-domain. Class III SLRPs contain six carboxyl LRRs and include mimecan, epiphycan and opticin.

Functional studies from mouse knockouts for class I and II members, such as decorin, biglycan, lumecan and fibromodulin, showed that the SLRP-deficient mice displayed a wide array of defects attributable to abnormal collagen fibrillogenesis suggesting that these SLRPs play important roles in establishing and maintaining the collagen matrix (Ameye, L. and Young, M. F., Glycobiology 12 (2002) 107R-116R). Deficiency of class III mimecan also caused collagen fibril abnormalities (Tasheva, E. S. et al., MoI. Vis. 8 (2002) 407-415).

Mimecan is a multifunctional component of the extracellular matrix. It binds to a variety of other proteins (IGF2, IKBKG, IFNB1, INSR, CHUK, IKBKB, NFKBIA, IL1 5, Cd3, retinoic acid, APP, TNF, lipopolysaccharide, c-abl oncogene 1, receptor tyrosine kinase, v-src sarcoma viral oncogene). These diverse binding activities may account for the ability of mimecan to exert diverse functions in many tissues.

Mimecan has been found in cornea, bone, skin and further tissues. Its expression pattern is altered in different pathological conditions. Despite the increasing amount of data on the biological role of mimecan its function is still not clear. Mimecan has been shown to be involved in regulating collagen fibrillogenesis, a process essential in development, tissue repair, and metastasis (Tasheva et al., Mol. Vis. 8 (2002) 407-415). It plays a role in bone formation in conjunction with TGF-beta-1 or TGF-beta-2.

In an aspect of the invention, a method for establishing an aid for assessing whether a subject shall be subjected to an imaging based diagnostic assessment or for assessing whether a subject suffers from abnormal MFS, is contemplated, said method comprising:

a) determining the amount of at least one marker selected from the group consisting of a cardiac Troponin and/or FGF-23, Vitamin D by (i) bringing the sample into contact with a detection agent that specifically binds to said cardiac Troponin for a time sufficient to allow for the formation of a complex of the said detection agent and said cardiac Troponin, and/or bringing the sample into contact with a detection agent that specifically binds to FGF-23 for a time sufficient to allow for the formation of a complex of the said detection agent and FGF-23 (ii) measuring the amount(s) of the formed complex(es), wherein the said amount(s) of the formed complex(es) is(are) proportional to the amount(s) of the cardiac Troponin and/or FGF-23, and (iii) transforming the amount(s) of the formed complex(es) into an amount (into amounts) of the cardiac Troponin and/or FGF-23 reflecting the amount(s) of the cardiac Troponin and/or FGF-23 present in the sample;

b) comparing said amount(s) to a reference (to references); and c) establishing an aid for assessing whether a subject shall be subjected to an imaging based diagnostic assessment or for diagnosing abnormal MFS based on the result of the comparison made in step b).

In another aspect of the invention, a system for establishing an aid for assessing whether a subject shall be subjected to an imaging based diagnostic assessment or for diagnosing abnormal MFS, is contemplated, comprising:

a) an analyzer unit configured to bringing the sample into contact with a detection agent that specifically binds to a cardiac Troponin, for a time sufficient to allow for the formation of a complex of the said detection agent and cardiac Troponin from the sample and/or with a detection agent that specifically binds to FGF-23 for a time sufficient to allow for the formation of a complex of the said detection agent and FGF-23 from the sample (and, optionally, if FGF-23 is determined, with a detection agent that specifically binds to vitamin D for a time sufficient to allow for the formation of a complex of the said detection agent and vitamin D from the sample, b) an analyzer unit configured to measure the amount(s) of the formed complex(es), wherein the said amount(s) of the formed complex(es) is (are) proportional to the amount(s) of the cardiac Troponin and/or FGF-23 (and, optionally, vitamin D), c) a computing device having a processor and in operable communication with said analysis units, and d) a non-transient machine readable media including a plurality of instructions executable by the processor, the instructions, when executed transform the amount of the formed complex(es) into an amount (into amounts) of the cardiac Troponin and/or FGF-23 (and, optionally, vitamin D) reflecting the amount(s) of the cardiac Troponin and/or FGF-23 (and optionally vitamin D) in the sample, compare said amount(s) to a reference (to references), and establish an aid for assessing whether a subject shall be subjected to an imaging based diagnostic assessment or for diagnosing abnormal MFS based on the result of said comparison to said reference(s).

A suitable detection agent may be, in an aspect, an antibody which specifically binds to the marker, i.e. antibody which specifically binds to a cardiac troponin or an antibody which specifically binds to FGF-23, in a sample of a subject to be investigated by the method of the invention. Another detection agent that can be applied, in an aspect, may be an aptamere which specifically binds to the cardiac Troponin or FGF-23. In yet another aspect the, sample is removed from the complex formed between the detection agent and the at least prior to the measurement of the amount of formed complex. Accordingly, in an aspect, the detection agent may be immobilized on a solid support. In yet an aspect, the sample can be removed from the formed complex on the solid support by applying a washing solution. The formed complex shall be proportional to the amount of the marker present in the sample. It will be understood that the specificity and/or sensitivity of the detection agent to be applied defines the degree of proportion of the marker comprised in the sample which is capable of being specifically bound. Further details on how the determination can be carried out are also found elsewhere herein. The amount of formed complex shall be transformed into an amount of at least one marker reflecting the amount indeed present in the sample. Such an amount, in an aspect, may be essentially the amount present in the sample or may be, in another aspect, an amount which is a certain proportion thereof due to the relationship between the formed complex and the amount present in the original sample.

In yet an aspect of the aforementioned method, step a) may be carried out by an analyzer unit, in an aspect, an analyzer unit as defined elsewhere herein.

In an aspect of the method of the invention, the amount(s) determined in step a) is (are) compared to a reference. In an aspect, the reference is a reference as defined elsewhere herein. In yet another aspect, the reference takes into account the proportional relationship between the measured amount of complex and the amount present in the original sample. Thus, the references applied in an aspect of the method of the invention are artificial references which are adopted to reflect the limitations of the detection agent that has been used. In another aspect, said relationship can be also taken into account when carrying out the comparison, e.g., by including a normalization and/or correction calculation step for the determined amount prior to actually comparing the value of the determined amount and the reference. Again, the normalization and/or correction calculation step for the determined amount adopts the comparison step such that the limitations of the detection agent that has been used are reflected properly. In an aspect, the comparison is carried out automatically, e.g., assisted by a computer system or the like.

The aid for assessing whether a subject shall be subjected to an imaging based assessment is established based on the comparison carried out in step b) by allocating the subject into a group of subjects that shall be subjected to said assessment, or a group of subjects that shall be not subjected to said assessment. The aid for diagnosing abnormal MFS is established based on the comparison carried out in step b) by allocating the subject into a group of subjects suffering from abnormal MFS, or a group of subjects not suffering from abnormal MFS. As discussed elsewhere herein already, the allocation of the investigated subject must not be correct in 100% of the investigated cases. Moreover, the groups of subjects into which the investigated subject is allocated are artificial groups in that they are established based on statistical considerations, i.e. a certain preselected degree of likelihood based on which the method of the invention shall operate. In an aspect of the invention, the aid is established automatically, e.g., assisted by a computing device or the like, as described and disclosed herein.

In an aspect of the method of the invention, said method further comprises a step of recommending and/or managing the subject according to the result established in step c).

In an aspect of the aforementioned method, steps b) and/or c) are carried out by one or more analyzer units as set forth elsewhere herein.

The present invention also relates to the use of i) a cardiac Troponin and/or FGF-23 or ii) of a detection agent which specifically binds to a cardiac Troponin and/or of a detection agent which specifically binds to FGF-23, in a sample of a subject for assessing whether a subject shall be subjected to an imaging based diagnostic assessment.

If FGF-23 is used, the use may further comprise the use of vitamin D. If a detection agent which specifically binds to FGF-23, the use may further comprise the use of a detection agent which specifically binds to vitamin D Further, a ratio between FGF-23 and vitamin D may be calculated.

The present invention also relates to the use of i) a cardiac Troponin and/or FGF-23 (and, optionally vitamin D) or ii) of a detection agent which specifically binds to a cardiac Troponin and/or of a detection agent which specifically binds to FGF-23 (and, optionally, of a detection agent which specifically binds to vitamin D) for the manufacture of a pharmaceutical or diagnostic composition for assessing whether a subject shall be subjected to an imaging based diagnostic assessment.

The present invention also relates to the use of i) a cardiac Troponin and/or FGF-23 or ii) of a detection agent which specifically binds to a cardiac Troponin and/or of a detection agent which specifically binds to FGF-23, in a sample of a subject for diagnosing abnormal MFS.

The present invention also relates to the use of i) a cardiac Troponin and/or FGF-23 (and, optionally vitamin D) or ii) of a detection agent which specifically binds to a cardiac Troponin and/or of a detection agent which specifically binds to FGF-23 (and, optionally, of a detection agent which specifically binds to vitamin D) for the manufacture of a pharmaceutical or diagnostic composition for diagnosing whether a subject suffers from abnormal MFS. A preferred detection agent is an antibody which specifically binds to the marker to be measured.

If FGF-23 is used, the use may further comprise the use of vitamin D. If a detection agent which specifically binds to FGF-23 is used, the use may further comprise the use of a detection agent which specifically binds to vitamin D. Further, a ratio between FGF-23 and vitamin D may be calculated.

The present invention also relates to the use of i) FGF-23 and/or IGFBP7 (and optionally of a cardiac Troponin and/or a brain natriuretic peptide) or ii) of a detection agent which specifically binds to FGF-23, and/or a detection agent which specifically binds to IGFBP7 (and optionally a detection agent which specifically binds to a cardiac Troponin and a detection agent which specifically binds to a brain natriuretic peptide) in a sample of a subject for predicting the risk of mortality and/or of a cardiovascular event.

The present invention also relates to the use of i) FGF-23 and/or IGFBP7 (and optionally of a cardiac Troponin and/or a brain natriuretic peptide) or ii) of a detection agent which specifically binds to FGF-23, and/or a detection agent which specifically binds to IGFBP7 (and optionally a detection agent which specifically binds to a cardiac Troponin and a detection agent which specifically binds to a brain natriuretic peptide) for the manufacture of a pharmaceutical or diagnostic composition for predicting the risk of mortality and/or of a cardiovascular event.

If FGF-23 is used, the use may further comprise the use of vitamin D. If a detection agent which specifically binds to FGF-23 is used, the use may further comprise the use of a detection agent which specifically binds to vitamin D. Further, a ratio between FGF-23 and vitamin D may be calculated.

The present invention also relates to the use of i) endostatin and a BNP-type peptide or ii) of a detection agent which specifically binds to endostatin and/or of a detection agent which specifically binds to a BNP-type peptide, in a sample of a subject having a preserved left ventricular ejection fraction for diagnosing an early stage of LVH.

The present invention also relates to the use of i) endostatin and a BNP-type peptide ii) of a detection agent which specifically binds to endostatin and/or of a detection agent which specifically binds to a BNP-type peptide for the manufacture of a pharmaceutical or diagnostic composition for diagnosing whether a subject having a preserved left ventricular ejection fraction for diagnosing an early stage of LVH. A preferred detection agent is an antibody which specifically binds to the marker to be measured.

The present invention also relates to the use of i) endostatin and a cardiac Troponin or ii) of a detection agent which specifically binds to endostatin and of a detection agent which specifically binds to a cardiac Troponin, in a sample of a subject having a preserved left ventricular ejection fraction for diagnosing an early stage of LVH.

The present invention also relates to the use of i) endostatin and a cardiac Troponin or ii) of a detection agent which specifically binds to endostatin and of a detection agent which specifically binds to a cardiac Troponin for the manufacture of a pharmaceutical or diagnostic composition for diagnosing an early stage of LVH in a subject having a preserved left ventricular ejection fraction. A preferred detection agent is an antibody which specifically binds to the marker to be measured.

The present invention also relates to the use of i) endostatin, a brain natriuretic peptide and a cardiac Troponin or ii) of a detection agent which specifically binds to a endostatin, of a detection agent which specifically binds to a BNP-type peptide, and of a detection agent which specifically binds to a cardiac Troponin, in a sample of a subject having a preserved left ventricular ejection fraction for diagnosing an early stage of LVH.

The term "detection agent" as used herein refers to an agent that is capable of specifically recognizing and binding to the biomarker polypeptide(s) present in a sample. The term is used inter-changeably with the term "ligand" herein. Moreover, the said agent shall allow for direct or indirect detection of the complex formed by the said agent and the biomarker. Direct detection can be achieved by including into the agent a detectable label. Indirect labeling may be achieved by a further agent that specifically binds to the complex comprising the biomarker and the detection agent wherein the said further agent is than capable of generating a detectable signal. Suitable compounds which can be used as detection agents are well known in the art. Preferably, the detection agent is an antibody, in particular a monoclonal antibody, or aptamere which specifically binds to the biomarker as referred to herein. The term "antibody" has been described elsewhere herein.

According to a preferred embodiment of the present invention, a device adapted for carrying out the method of the invention is provided comprising
  a) an analyzer unit comprising a detection agent which specifically binds to a cardiac troponin, and/or a detection agent which specifically binds to FGF-23 (and, optionally, if FGF-23 is determined, a detection agent which specifically binds to vitamin D), said unit being adapted for determining the amount(s) of the marker(s) in a sample of a subject; and
  b) an analyzer unit for comparing the determined amount (s) with reference amount(s), whereby it is assessed whether the subject shall be subjected to an imaging based assessment, said unit comprising a database with a reference amount (or amounts) and a computer-implemented algorithm for carrying out the comparison.

Preferred reference amounts and algorithms are disclosed elsewhere herein.

According to a preferred embodiment of the present invention, a device adapted for carrying out the method of the invention is provided comprising
  a) an analyzer unit comprising a detection agent which specifically binds to a cardiac troponin, and/or a detection agent which specifically binds to FGF-23 (and, optionally, if FGF-23 is determined, a detection agent which specifically binds to vitamin D), said unit being adapted for determining the amount(s) of the marker(s) in a sample of a subject; and
  b) an analyzer unit for comparing the determined amount (s) with reference amount(s), whereby it is assessed whether the subject suffers from abnormal MFS, said unit comprising a database with a reference amount (or amounts) and a computer-implemented algorithm for carrying out the comparison.

According to another preferred embodiment of the present invention, a device adapted for carrying out the method of the invention is provided, said device comprising
  a) an analyzer unit comprising a detection agent which specifically binds to IGFBP7 and/or detection agent which specifically binds to FGF-23 (and optionally a detection agent which specifically binds to cardiac Troponin and/or detection agent which specifically binds to a brain natriuretic peptide), said unit being adapted for determining the amount(s) of the marker(s) in a sample of a subject; and
  b) an analyzer unit for comparing the determined amount (s) with reference amount(s), whereby the risk of mortality and/or of a cardiovascular event is predicted, said unit comprising a database with a reference amount (or amounts) and a computer-implemented algorithm for carrying out the comparison.

According to another preferred embodiment of the present invention, a device adapted for carrying out the method of the invention is provided, said device comprising
  a) an analyzer unit comprising i) a detection agent which specifically binds to endostatin and ii) a detection agent which specifically binds to a BNP-type peptide and/or a detection agent which specifically binds to a cardiac Troponin, said unit being adapted for determining the amounts of i) endostatin and ii) the BNP-type peptide and/or the cardiac Troponin in a sample from a subject having a preserved LVEF; and
  b) an analyzer unit for comparing the determined amount (s) with reference amounts, whereby early left ventricular hypertrophy is diagnosed, said unit comprising a database with reference amounts for the markers and a computer-implemented algorithm for carrying out the comparison.

Preferred reference amounts and algorithms are disclosed elsewhere herein.

If FGF-23 and vitamin D are determined, a ratio shall be calculated as set forth elsewhere herein, and shall be compared to a reference ratio. In this case, the analyzer unit as set forth in the context of the aforementioned devices shall (also) allow for calculating a ratio between FGF-23 and vitamin D Further, the database shall comprise values for reference ratios.

A preferred embodiment of the instant disclosure includes a system for assessing whether a subject shall be subjected to an imaging based assessment, or for diagnosing abnormal MFS as set forth elsewhere herein. Examples of systems include clinical chemistry analyzers, coagulation chemistry analyzers, immunochemistry analyzers, urine analyzers, nucleic acid analyzers, used to detect the result of chemical or biological reactions or to monitor the progress of chemical or biological reactions. More specifically, exemplary systems of the instant disclosure may include Roche Elecsys™ Systems and Cobas® e Immunoassay Analyzers, Abbott Architect™ and Axsym™ Analyzers, Siemens Centaur™ and Immulite™ Analyzers, and Beckman Coulter UniCel™ and Acess™ Analyzers, or the like.

Embodiments of the system may include one or more analyzer units utilized for practicing the subject disclosure. The analyzer units of the system disclosed herein are in operable communication with the computing device disclosed herein through any of a wired connection, Bluetooth, LANS, or wireless signal, as are known. Additionally, according to the instant disclosure, an analyzer unit may comprise a stand-alone apparatus, or module within a larger instrument, which performs one or both of the detection, e.g. qualitative and/or quantitative evaluation of samples for diagnostic purpose. For example, an analyzer unit may perform or assist with the pipetting, dosing, mixing of samples and/or reagents. An analyzer unit may comprise a reagent holding unit for holding reagents to perform the assays. Reagents may be arranged for example in the form of containers or cassettes containing individual reagents or group of reagents, placed in appropriate receptacles or positions within a storage compartment or conveyor. Detection reagents may also be in immobilized form on a solid support which are contacted with the sample. Further, an analyzer unit may include a process and/or detection component which is optimizable for specific analysis.

According to some embodiments, an analyzer unit may be configured for optical detection of an analyte, for example a marker, with a sample. An exemplary analyzer unit configured for optical detection comprises a device configured for converting electro-magnetic energy into an electrical signal, which includes both single and multi-element or array optical detectors. According to the present disclosure, an optical detector is capable of monitoring an optical electromagnetic signal and providing an electrical outlet signal or response signal relative to a baseline signal indicative of the presence and/or concentration of an analyte in a sample being located in an optical path. Such devices may also include, for example, photodiodes, including avalanche photodiodes, pho-totransistors, photoconductive detectors, linear sensor arrays, CCD detectors, CMOS detectors, including CMOS array detectors, photomultipliers, and photomultiplier arrays. According to certain embodiments, an optical detector, such as a photodiode or photomultiplier, may contain additional signal conditioning or processing electronics. For example, an optical detector may include at least one pre-amplifier, electronic filter, or integrated circuit. Suitable pre-preamplifiers include, for example, integrating, transimpedance, and current gain (current mirror) pre-amplifiers.

Additionally, one or more analyzer unit according to the instant disclosure may comprise a light source for emitting light. For example, a light source of an analyzer unit may consist of at least one light emitting element (such as a light emitting diode, an electric powered radiation source such as an incandescent lamp, an electroluminescent lamp, a gas discharge lamp, a high-intensity discharge lamp, a laser) for measuring analyte concentrations with a sample being tested or for enabling an energy transfer (for example, through florescent resonance energy transfer or catalyzing an enzyme).

Further, an analyzer unit of the system may include one or more incubation units (for example, for maintaining a sample or a reagent at a specified temperature or temperature range). In some embodiments, an analyzer unit may include a thermocycler, include a real-time thermocycler, for subjecting a sample to repeated temperature cycles and monitoring a change in the amount of an amplification product with the sample.

Additionally, an analyzer unit of the system disclosed herein may comprise, or be operationally connected to, a reaction vessel or cuvette feeding unit. Exemplary feeding units include liquid processing units, such as a pipetting unit, to deliver samples and/or reagents to the reaction vessels. The pipetting unit may comprise a reusable washable needle, e.g. a steel needle, or disposa-ble pipette tips. The analyzer unit may further comprise one or more mixing units, for example a shaker to shake a cuvette comprising a liquid, or a mixing paddle to mix liquids in a cuvette, or reagent container.

It follows from the above that according to some embodiments of the instant disclosure, portions of some steps of methods disclosed and described herein may be performed by a computing device. A computing device may be a general purpose computer or a portable computing device, for example. It should also be understood that multiple computing devices may be used together, such as over a network or other methods of transferring data, for performing one or more steps of the methods disclosed herein. Exemplary computing devices include desktop computers, laptop computers, personal data assistants ("PDA"), such as BLACKBERRY brand devices, cellular devices, tablet computers, servers, and the like. In general, a computing device comprises a processor capable of executing a plurality of instructions (such as a program of software).

A computing device has access to a memory. A memory is a computer readable medium and may comprise a single storage device or multiple storage devices, located either locally with the computing device or accessible to the computing device across a network, for example. Computer-readable media may be any available media that can be accessed by the computing device and includes both volatile and non-volatile media. Further, computer readable-media may be one or both of removable and non-removable media. By way of example, and not limitation, computer-readable media may comprise computer storage media. Exemplary computer storage media includes, but is not limited to, RAM, ROM, EEPROM, flash memory or any other memory tech-nology, CD-ROM, Digital Versatile Disk (DVD) or other optical disk storage, magnetic cassettes, magnetic tape, magnetic disk storage or other magnetic storage devices, or any other medium which can be used for storing a plurality of instructions capable of being accessed by the computing device and executed by the processor of the computing device.

According to embodiments of the instant disclosure, software may include instructions which, when executed by a processor of the computing device, may perform one or more steps of the methods disclosed herein. Some of the instructions may be adapted to produce signals that control operation of other machines and thus may operate through those control signals to transform materials far removed from the computer itself. These descriptions and representations are the means used by those skilled in the art of data processing, for example, to most effectively convey the substance of their work to others skilled in the art.

The plurality of instructions may also comprise an algorithm which is generally conceived to be a self-consistent sequence of steps leading to a desired result. These steps are those requiring physical manipulations of physical quantities. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as values, characters, display data, numbers, or the like as a reference to the physical items or manifestations in which such signals are embodied or expressed. It should be borne in mind, however, that all of these and similar terms are to be associated with the appropriate physical quantities and are merely used here as convenient labels applied to these quantities. According to some embodiments of the instant disclosure, an algorithm for carrying out a comparison between a determined amount of one or more markers disclosed herein, and a suitable reference, is embodied and performed by executing the instructions. The results may be given as output of parametric diagnostic raw data or as absolute or relative amounts. According to various embodiments of the system disclosed herein, a "diagnosis" may be provided by the computing device of a system disclosed herein based on said comparison of the calculated "amount" to a reference or a threshold. For example, a computing device of a system may provide an indicator, in the form of a word, symbol, or numerical value which is indicative of a particular diagnosis.

The computing device may also have access to an output device. Exemplary output devices include fax machines, displays, printers, and files, for example. According to some embodiments of the present disclosure, a computing device may perform one or more steps of a method disclosed herein, and thereafter provide an output, via an output device, relating to a result, indication, ratio or other factor of the method.

Finally, the invention pertains to a kit adapted for carrying out a method of the present invention comprising a detection agent which specifically binds to a cardiac troponin, and/or a detection agent which specifically binds to FGF-23, reference standards as well as instructions for carrying out the said method.

In a preferred embodiment, the kit may further comprise, a detection agent which specifically binds to vitamin D.

The term "kit" as used herein refers to a collection of the aforementioned components, preferably, provided in separately or within a single container. The container also comprises instructions for carrying out the method of the present invention. These instructions may be in the form of a manual or may be provided by a computer program code which is capable of carrying out the comparisons referred to in the methods of the present invention and to establish a diagnosis accordingly when implemented on a computer or a data processing device. The computer program code may be provided on a data storage medium or device such as a optical storage medium (e.g., a Compact Disc) or directly on a computer or data processing device. Further, the kit shall comprise at least one standard for a reference as defined herein above.

In some embodiments, a kit disclosed herein includes at least one component or a packaged combination of components for practicing a disclosed method. By "packaged combination" it is meant that the kits provide a single package that contains a combination of one or more components, such as probes (for example, an antibody), controls, buffers, reagents (for example, conjugate and/or substrate) instructions, and the like, as disclosed herein. A kit containing a single container is also included within the definition of "packaged combination." In some embodiments, the kits include at least one probe, for example an antibody (having specific affinity for an epitope of a biomarker as disclosed herein. For example, the kits may include an antibody that is labelled with a fluorophore or an antibody that is a member of a fusion protein. In the kit, the probe may be immobilized, and may be immobilized in a specific conformation. For example, an immobilized probe may be provided in a kit to specifically bind target protein, to detect target protein in a sample, and/or to remove target protein from a sample.

According to some embodiments, kits include at least one probe, which may be immobilized, in at least one container. Kits may also include multiple probes, optionally immobilized, in one or more containers. For example, the multiple probes may be present in a single container or in sep-arate containers, for example, wherein each container contains a single probe.

In some embodiments, a kit may include one or more non-immobilized probe and one or more solid support that does or does not include an immobilized probe. Some such embodiments may comprise some or all of the reagents and supplies needed for immobilizing one or more probes to the solid support, or some or all of the reagents and supplies needed for binding of immobilized probes to specific proteins within a sample.

In certain embodiments, a single probe (including multiple copies of the same probe) may be immobilized on a single solid support and provided in a single container. In other embodiments, two or more probes, each specific for a different target protein or a different form of a single target protein (such as a specific epitope), a provided in a single container. In some such embodiments, an immobilized probe may be provided in multiple different containers (e.g., in single-use form), or multiple immobilized probes may be provided in multiple different containers. In further embodiments, the probes may be immobilized on multiple different type of solid supports. Any combination of immobilized probe(s) and container(s) is contemplated for the kits disclosed herein, and any combination thereof may be selected to achieve a suitable kit for a desired use.

A container of the kits may be any container that is suitable for packaging and/or containing one or more components disclosed herein, including for example probes (for example, an antibody), controls, buffers, and reagents (for example, conjugate and/or substrate). Suitable materials include, but are not limited to, glass, plastic, cardboard or other paper product, wood, metal, and any alloy thereof. In some embodiments, the container may completely encase an immobilized probe(s) or may simply cover the probe to minimize contamination by dust, oils, etc., and expose to light. In some further embodiments, he kits may comprise a single container or multiple containers, and where multiple containers are present, each container may be the same as all other containers, different than others, or different than some but not all other containers.

In the following, preferred embodiments of the invention are listed. The definitions and explanations given herein above and in the claims apply mutatis mutandis.

1. A method for assessing whether a subject shall be subjected to an imaging based diagnostic assessment comprising the steps of
    a) determining the amount(s) of a cardiac Troponin and/or Fibroblast Growth Factor 23 (FGF-23) in a sample from the subject, and
    b) comparing the, thus, determined amount(a) to a reference amount (reference amounts), whereby it is assessed whether the subject shall be subjected to an imaging based diagnostic assessment.
2. The method of embodiment 1, wherein the subject suffers from hypertension.
3. The method of embodiments 1 and 2, wherein the subject does not suffer from left ventricular hypertrophy, in particular wherein the subject has a normal left ventricular mass.
4. The method any one of embodiments 1 to 3, wherein the imaging based diagnostic assessment is echocardiography or magnetic resonance imaging.
5. The method of any one of embodiments 1 and 4, wherein the imaging based diagnostic assessment is for diagnosing diastolic and/or systolic dysfunction, in particular for diagnosing abnormal midwall fractional shortening.
6. The method of any one of embodiments 1 to 5, wherein an increased amount in the sample from the subject as compared to the reference amount indicates that the subject shall be subjected to imaging based diagnostic assessment.
7. The method of any one of embodiments 1 to 6, wherein a decreased amount in the sample from the subject as compared to the reference amount indicates that the subject shall not be subjected to imaging based diagnostic assessment.
8. The method of any one of embodiment 1 to 7, wherein the reference amount is a calculated reference amount.
9. The method of any one of embodiments 1 to 7, wherein the reference amount is the amount of the a cardiac Troponin and/or of FGF-23 in a first sample that has been obtained from the subject prior to the sample as set forth in step a) of embodiment 1 ("second sample").
10. The method of embodiment 9, wherein the first sample has been obtained 6 to 18 months prior to the second sample.
11. The method of embodiments 9 or 10, wherein an amount of a cardiac Troponin, in particular, of Troponin T, in the second sample that is at least 10%, or, in particular, at least 25% larger than the amount in the first sample, and/or wherein an amount of FGF-23 in the second sample, that is at least 5%, or, in particular, at least 10% larger than the amount in the first sample is indicative for a subject who shall be subjected to an imaging based diagnostic assessment.
12. The method of any one of embodiments 9 to 11, wherein the subject did not suffer from abnormal MFS at the time at which the first sample has been obtained.
13. The method of any one of embodiments 9 to 12, wherein the subject suffered from hypertension at the time at which the first sample was obtained.
14. A method for diagnosing abnormal midwall fractional shortening (MFS) in a subject comprising the steps of
a) determining the amount of a cardiac Troponin and/or Fibroblast Growth Factor 23 (FGF-23) in a sample from the subject, and
b) comparing the, thus, determined amount to a reference amount, whereby abnormal midwall fractional shortening is diagnosed.
15. The method of embodiment 14, wherein the subject does not suffer from left ventricular hypertrophy, in particular wherein the subject has a normal left ventricular mass.
16. The method of embodiments 14 and 15, wherein an increased amount in the sample from the subject as compared to the reference amount indicates that the subject suffers from abnormal MFS, and wherein a decreased amount in the sample from the subject as compared to the reference amount indicates that the subject does not suffer from abnormal MFS.
17. The method of any one of embodiments 1 to 16, wherein the sample is a blood, serum or plasma sample.
18. The method of any of embodiments 1 to 17, wherein the amounts of both a cardiac Troponin and FGF-23 are determined.
19. The method of any one of embodiments 1 to 18, wherein, if the amount of FGF-23 is determined, the method comprises the determination of the amount of vitamin D in step a) in addition to the determination of FGF-23, the calculation of a ratio between the amount of FGF-23 to the amount of vitamin D in a further step a1), and the comparison of the, thus, calculated ratio with a reference ratio.
20. The method of any one of embodiments 1 to 19, wherein the subject does not suffer from impaired renal function.
21. The method of any one of embodiments 1 to 20, wherein the subject does not have increased NT-proBNP levels, in particular in a blood, serum or plasma sample.
22. Use of i) a cardiac Troponin and/or FGF-23 or ii) of a detection agent which specifically binds to a cardiac Troponin and/or of a detection agent which specifically binds to FGF-23, in a sample of a subject for assessing whether the subject shall be subjected to an imaging based diagnostic assessment.
23. A device adapted for carrying out the method of embodiment 1 to 13 comprising
a) an analyzer unit comprising a detection agent which specifically binds to a cardiac troponin, and/or a detection agent which specifically binds to FGF-23 (and, optionally, if FGF-23 is determined, a detection agent which specifically binds to vitamin D), said unit being adapted for determining the amount(s) of the marker(s) in a sample of a subject; and
b) an analyzer unit for comparing the determined amount (s) with reference amount(s), whereby it is assessed whether the subject shall be subjected to an imaging based assessment, said unit comprising a database with a reference amount (or amounts) and a computer-implemented algorithm for carrying out the comparison.

All references cited in this specification are herewith incorporated by reference with respect to their entire disclosure content and the disclosure content specifically mentioned in this specification.

The following Examples shall merely illustrate the invention. They shall not be construed, whatsoever, to limit the scope of the invention.

Example 1: Patient Cohort

The relationship between plasma levels of FGF-23 (ELISA, Immutopics), total 25-hydroxyvitamin D (ECLIA, Roche Diagnostics), IFGBP7, endostatin, mimecan and 2 cardiac markers (hs-cTnT and NT-proBNP, Roche Elecsys assays) and elevated LV mass/BSA (>95 g/m$^2$ for women, >115 for men), subnormal midwall fractional shortening (MFS<15%) and mortality was examined in 2001 elderly people (mean age 73±5 years, 48% women), resident in central Italy (the PREDICTOR study). The subjects were divided into 4 categories according to normal values of LV mass index and MF. The markers were determined in plasma samples. Data on all-cause mortality were available for a subgroup of 1200 subjects after a median follow-up of 47 months (86 deaths).

Three markers (Endostatin, IGFBP7 Mimecan/Osteoglycin) were examined in 550 elderly subjects selected from the 2001 subjects aged 65-84 years of the epidemiological study PREDICTOR. This subcohort comprises 50 normal subjects, 150 subject in AHA/ACC stage A, 300 subjects in stage B. Median follow-up was 47 months (21 deaths).

The subjects were divided into 4 categories according to normal values of LV mass index and MFS
a) subjects with normal LV mass index (LV mass/BSA≤95 g/m$^2$ for women and ≤115 g/m$^2$ for men) AND normal MFS (≥15%)
b) subjects with normal LV mass index (LV mass/BSA≤95 g/m$^2$ for women and ≤115 g/m$^2$ for men) AND abnormal MFS (<15%)
c) subjects with elevated LV mass index (LV mass/BSA>95 g/m$^2$ for women and >115 g/m$^2$ for men) AND normal MFS (≥15%)

d) subjects with elevated LV mass index (LV mass/BSA>95 g/m² for women and >115 g/m² for men) AND abnormal MFS (<15%)

Example 2: Assays

Troponin T was determined using Roche's electrochemiluminescence ELISA sandwich test Elecsys Troponin T hs (high sensitive) STAT (Short Turn Around Time) assay. The test employs two monoclonal antibodies specifically directed against human cardiac troponin T. The antibodies recognize two epitopes (amino acid position 125-131 and 136-147) located in the central part of the cardiac troponin T protein, which consists of 288 amino acids. The hs-TnT assay allows a measurement of troponin T levels in the range of 3 to 10000 pg/mL.

NT-proBNP was determined using Roche's electrochemiluminescence ELISA sandwich test Elecsys proBNP II STAT (Short Turn Around Time) assay. The test employs two monoclonal antibodies which recognize epitopes located in the N-terminal part (1-76) of proBNP (1-108).

Human FGF-23 was determined by used the (C-Term) ELISA Kit from Immutopics Inc., Cat. Number 60-6100, 2nd Generation Enzyme-Linked ImmunoSorbent Assay (ELISA) for the Determination of Human Fibroblast Growth Factor 23 Levels in Plasma or Cell Culture Media). This 2nd generation Human FGF-23 (C-Term) ELISA Kit is a two-site enzyme-linked immunosorbent assay (ELISA) for the measurement of FGF-23 in plasma or cell culture media. Two affinity purified goat polyclonal antibodies have been selected to detect epitopes within the carboxyl-terminal (C-Term) portion of FGF-23. One antibody is biotinylated for capture and the other antibody is conjugated with the enzyme horseradish peroxidase (HRP) for detection. These antibodies bind to both the intact molecule and large carboxyl terminal fragments of human FGF-23. A sample containing human FGF-23 is incubated simultaneously with the biotinylated capture antibody and the HRP conjugated antibody in a streptavidin coated microtiter well. FGF-23 contained in the sample is immunologically bound by the capture antibody and the detection antibody to form a "sandwich" complex. At the end of this incubation period, the well is washed to remove any unbound antibody and other components. The enzyme bound to the well is incubated with a substrate solution in a timed reaction and then measured in a spectrophotometric microtiter plate reader. The enzymatic activity of the antibody complex bound to the well is directly proportional to the amount of FGF-23 in the sample. A standard curve is generated by plotting the absorbance versus the respective FGF-23 concentration for each standard on linear or logarithmic scales. The concentration of human FGF-23 in the samples is determined directly from this curve.

For detection of mimecan in human serum or plasma, a sandwich ELISA was used. For capture and detection of the antigen, aliquots of an anti-mimecan polyclonal antibody from R&D Systems (Catalogue number: AF 2660) are conjugated with biotin and digoxygenin, respectively. Streptavidin-coated 96-well microtiter plates are incubated with 100 µl biotinylated anti-mimecan polyclonal antibody for 60 min at 0.2 µg/ml in 1×PBS solution. After incubation, plates are washed three times with 1×PBS+0.02% Tween-20, blocked with PBS+2% BSA (bovine serum albumen) for 45 min and then washed again three times with 1×PBS+0.02% Tween-20. Wells are then incubated for 1 h with 100 µl of either a serial dilution of the recombinant mimecan as standard antigen or with diluted serum or plasma samples (1:5 in 1×PBS+1% BSA) from patients or control individuals, respectively. After binding of mimecan, plates are washed three times with 1×PBS+0.02% Tween-20. For specific detection of bound mimecan, wells are incubated with 100 µl of digoxigenylated anti-mimecan polyclonal antibody for 45 min at 0.2 µg/ml in 1×PBS+1% BSA. Thereafter, plates are washed three times to remove unbound antibody. In a next step, wells are incubated with 100 µl of 75 mU/ml anti-digoxigenin-POD conjugates (Roche Diagnostics GmbH, Mannheim, Germany, Catalog No. 1633716) for 30 min in 1×PBS+1% BSA. Plates are subsequently washed six times with the same washing buffer as above. For detection of antigen-antibody complexes, wells are incubated with 100 µl ABTS solution (Roche Diagnostics GmbH, Mannheim, Germany, Catalog No. 11685767) and the optical density (OD) is measured after 15 min at 405 and 492 nm with an ELISA reader.

For measurement of endostatin in human serum or plasma, a commercially available sandwich ELISA (Quantikine Human Endostatin Immunoassay, Catalog Number DNSTO, R&D Systems) was used. Measurements are performed according to the instructions given by the manufacturer.

For detection of IGFBP7 in human serum or plasma, a sandwich ELISA was used. For capture and detection of the antigen, aliquots of an anti-IGFBP7 polyclonal antibody from R&D Systems (Catalogue number: AF 1334) was conjugated with biotin and digoxigenin, respectively.

Example 3: Results

Subtle Alterations of LV Geometry—Midwall Fractional Shortening

The results are shown in table 1. Median concentrations of hs-cTnT, NT-proBNP, FGF-23 and vitamin D were on average low. Median concentrations of hs-cTnT, Nt-proBNP and FGF-23/Vitamin D were higher in subjects with elevated LV mass and/or or subnormal MFS (for both, adjusted for sex and age). FGF-23 and vitamin D were significantly associated to LV mass independently of hs-cTnT.

TABLE 1

Categories of LV mass index/MFS

| | Categories of LV mass index/MFS | | | | |
|---|---|---|---|---|---|
| | Normal LVMI Normal MFS | Normal LVMI Abnormal MFS | Elevated LVMI Normal MFS | Elevated LVMI Abnormal MFS | P* |
| N | 918 (57.8) | 275 (17.3) | 189 (11.9) | 206 (13) | |
| Age (year) | 72.1 (4.8) | 73.3 (5.2) | 72.9 (4.9) | 74.3 (5.1) | <0.0001 |
| Females | 444 (48.4) | 108 (39.3) | 130 (68.8) | 120 (58.3) | 0.0525 |
| LV mass/BSA (g/m²) | 81.1 (14.1) | 88.0 (13.8) | 116.0 (18.0) | 125.7 (22.8) | <0.0001 |

TABLE 1-continued

Categories of LV mass index/MFS

| | Normal LVMI Normal MFS | Normal LVMI Abnormal MFS | Elevated LVMI Normal MFS | Elevated LVMI Abnormal MFS | P* |
|---|---|---|---|---|---|
| MFS (%) | 17.4 (1.6) | 13.5 (1.2) | 16.5 (1.3) | 12.8 (2.0) | P |
| Markers | | | | | |
| NT-proBNP | 78 | 80 | 124 | 182 | <0.0001 |
| Hs-cTnT | 4.3 | 5.9 | 5.48 | 8.5 | <0.0001 |
| Vitamin D [ng/ml] | 13.53 | 13.71 | 9.88 | 10.64 | 0.0021 |
| FGF-23 [relative units/ml] | 69.1 | 74.0 | 76.2 | 84.1 | <0.0001 |
| FGF-23/vitamin D# | 5.3 | 5.9 | 6.8 | 8.3 | <0.0001 |

*P adjusted for sex and age.
ratio between circulating levels of FGF-23 and vitamin D (calculated individually for each subject
NT-proBNP median concentrations were not increased in elderly subjects with normal LV mass index AND subnormal MFS versus elderly subjects with normal LV mass AND normal MFS.

In contrast median concentrations of hs-cTnT and the ratio of median concentrations of FGF-23/vitamin D were significantly increased by 37% and 11% in elderly subjects with normal LV mass index AND subnormal MFS versus elderly subjects with normal LV mass AND normal MFS.

Cardiac Troponin and FGF-23 levels are elevated in elderly subjects with subtle alterations of LV geometry and function (even before detectable alterations in LV geometry). Thus, the determination of these markers will help to identify an intermediate phenotype in the progression from hypertension to systolic or diastolic dysfunction before LVH becomes apparent (by Echo, MRI, ECG). The ratio of FGF-23/Vitamin D may be determined in addition. An increased level of a marker selected from cardiac Troponin, FGF-23 (preferably the ratio of FGF-23/vitamin D) relative to the respective reference level indicates that the patient suffers from MFS.

Mortality/Cardiovascular Events

NT-proBNP, hs-cTnT, vitamin D and FGF-23 were determined in 1202 subjects—with data to all—cause mortality. Median follow-up was 47 months [Q1-Q3 39-55]. The results are shown in the following table. Continuous data shown as mean±SD except for the circulating biomarkers (median [Q1-Q3]). Categorical data as n (%).

Markers according to survival status (decedents vs. alive)

| | All subjects (with data on mortality available) | Decedents (all-cause mortality) | Survivors | P |
|---|---|---|---|---|
| No. | 1202 | 86 | 1116 | |
| Biomarkers (Median [Q1- | | | | |
| hs-cTnT (ng/L) | 5.4 [3.0-9.7] | 10.0 [5.2-18.6] | 5.2 [3.0-9.2] | <0.001 |
| Hs-cTnT >3 ng/L (n, %) | 820 (68.6) | 70 (81.4) | 750 (67.6) | 0.008 |
| NT-proBNP (ng/L) | 90 [44-186] | 192 [108-441] | 85 [42-174] | <0.001 |
| Vitamin D (ng/mL) | 12.8 [7.2-20.5] | 8.8 [4.5-17.5] | 13.1 [7.4- | <0.001 |
| FGF-23 (RU/mL) | 74.9 [58.5-100.1] | 90.2 [66.4-137.0] | 74.3 [58-97.3] | <0.001 |

The following table provides a more comprehensive overview (and e.g. includes the clinical characteristics):

| | All subjects (with data on mortality available) | Decedents (all-cause mortality) | Survivors | P |
|---|---|---|---|---|
| No. (%) | 1202 | 86 | 1116 | |
| Age (year, mean ± SD) | 73 (5.0) | 75.1 (5.2) | 72.8 (5.0) | <0.0001 |
| Females (n, %) | 580 (48.3) | 36 (41.9) | 544 (48.7) | 0.218 |
| Normal | 134 (11.1) | 5 (5.8) | 129 (11.6) | <0.0001 |
| A | 249 (20.7) | 16 (18.6) | 233 (20.9) | |
| B | 737 (61.3) | 50 (58.1) | 687 (61.6) | |
| C | 82 (6.8) | 15 (17.4) | 67 (6.0) | |
| LV hypertrophy at ECG (n, %) | 76 (6.8) | 7 (9.9) | 69 (6.6) | 0.508 |
| MFS (%) | 13.7 (6.1) | 12.2 (6.4) | 13.8 (6.1) | 0.018 |
| Reduced MFS * (n, %) | 296 (29.6) | 32 (47.8) | 264 (28.3) | 0.001 |
| LVEF (n, %) | 66.3 (7.4) | 63.4 (8.1) | 66.5 (7.3) | <0.0001 |

|  | All subjects (with data on mortality available) | Decedents (all-cause mortality) | Survivors | P |
|---|---|---|---|---|
| Prevalence of HF (n, %) | 82 (7.1) | 15 (19.0) | 67 (6.2) | <0.0001 |
| Prevalence of diastolic dysfunction (n, %) | 553 (49.1) | 44 (57.9) | 509 (48.5) | 0.113 |
| hs-cTnT (ng/L) | 5.4 [3.0-9.7] | 10.0 [5.2-18.6] | 5.2 [3.0-9.2] | <0.001 |
| NT-proBNP (ng/L) | 90 [44-186] | 192 [108-441] | 85 [42-174] | <0.001 |
| Vitamin D (ng/mL) | 12.8 [7.2-20.5] | 8.8 [4.5-17.5] | 13.1 [7.4-20.7] | <0.001 |
| FGF-23 (RU/mL) | 74.9 [58.5-100.1] | 90.2 [66.4-137.0] | 74.3 [58-97.3] | <0.001 |

As can be seen from the table, 86 subjects (7.1%) died during the follow-up of about 4 years. The plasma concentrations of hs-cTnT, NT-proBNP and FGF-23 were higher in decedents while vitamin D was lower.

The following table provides an univariate Cox analyses for the association between biomarker concentrations and all-cause mortality (HR: Hazard Ratio)

|  | HR | p |
|---|---|---|
| NT-proBNP | 1.971 | <0.0001 |
| hs-cTnT | 2.650 | <0.0001 |
| Vitamin D | 0.585 | <0.0001 |
| FGF-23 | 2.081 | <0.0001 |

As can be seen from the table, NT-proBNP, hs-cTnT, vitamin D and FGF-23 are significantly associated with all-cause mortality at univariate analyses.

The following table provides a multivariable Cox analysis for the association between biomarker concentrations and all-cause mortality after adjustment.

|  | HR | p |
|---|---|---|
| NT-proBNP | 1.707 | <0.0001 |
| hs-cTnT | 2.102 | <0.0001 |
| Vitamin D | 0.684 | 0.016 |
| FGF-23 | 1.884 | <0.0001 |

Thus, higher circulating levels of FGF-23 (HR 1.88 [1.40-2.54], p<0.0001) and lower concentrations of vitamin D (HR 0.68 [0.50-0.93], p=0.02) were associated with all-cause mortality (86 deaths, 7.2%), after adjustment for demographical and clinical variables and for benchmark cardiac biomarkers (NT-proBNP or hs-cTnT).

Further, the markers IGBPB7, mimecan and endostatin were assayed in samples from 550 elderly subjects selected from the Predictor study. The results are shown in the following table. Continuous data shown as mean±S D except for the circulating biomarkers (median [Q1-Q3]). Categorical data as n (%).

Markers according to survival status (decedents vs. alive)

|  | All subjects (with data on mortality available) | Decedents (all-cause mortality) | Survivors | P (decedents vs. survivors) |
|---|---|---|---|---|
| No. | 511 | 21 | 490 | |
| Biomarkers (Median [Q1-Q3]) | | | | |
| hs-cTnT (ng/L) | 5.8 [3-9.5] | 14.9 [9.1-17.6] | 5.5 [3-8.9] | <0.001 |
| NT-proBNP (ng/L) | 95 [47-210] | 304 [170-959] | 90 [46-198] | <0.001 |
| IGFBP7 (ng/mL) | 99 [85-113] | 124 [106-143] | 98 [85-112] | <0.001 |
| Mimecan (ng/mL) | 72 [55-98] | 68 [61-92] | 72 [55-98] | 0.650 |
| Endostatin (ng/mL) | 164 [138-201] | 158 [150-200] | 164 [138-201] | 0.979 |

The following table provides a more comprehensive overview (and e.g. includes the clinical characteristics):

|  | All subjects (with data on mortality available) | Decedents (all-cause mortality) | Survivors | P (decedents vs. survivors) |
|---|---|---|---|---|
| No. (%) | 511 | 21 | 490 | |
| Age (year, mean ± SD) | 72.8 (5.1) | 76.0 (4.7) | 72.7 (5.1) | 0.004 |
| Females (n, %) | 248 (48.5) | 4 (19.0) | 244 (49.8) | 0.005 |
| ACC/AHA stage (%) | | | | |
| Normal | 44 (8.6) | 0 | 44 (9.0) | 0.060 |
| A | 138 (27.0) | 9 (42.9) | 129 (26.3) | |
| B | 282 (55.2) | 8 (38.1) | 274 (55.9) | |
| C | 47 (9.2) | 4 (19.0) | 43 (8.8) | |

|  | All subjects (with data on mortality available) | Decedents (all-cause mortality) | Survivors | P (decedents vs. survivors) |
| --- | --- | --- | --- | --- |
| Echocardiography/ECG findings |  |  |  |  |
| LV hypertrophy at ECG (n, %) | 50 (10.7) | 2 (11.1) | 48 (10.7) | 0.844 |
| MFS (%) | 14.0 (5.7) | 11.8 (6.8) | 14.1 (5.6) | 0.082 |
| LVEF (n, %) | 65.9 (7.9) | 60.9 (10.3) | 66.1 (7.8) | 0.007 |
| Prevalence of HF (n, %) | 47 (9.6) | 4 (22.2) | 43 (9.1) | 0.084 |
| Prevalence of diastolic dysfunction (n, %) | 196 (43.3) | 9 (56.3) | 187 (42.8) | 0.036 |
| IGFBP7 R&D (ng/mL) | 99 [85-113] | 124 [106-143] | 98 [85-112] | <0.001 |
| Mimecan (ng/mL) | 72 [55-98] | 68 [61-92] | 72 [55-98] | 0.650 |
| Endostatin (ng/mL) | 164 [138-201] | 158 [150-200] | 164 [138-201] | 0.979 |

Comment: As can be seen from the table the median of the LVEF was larger than 65%. The tested subjects, thus, did not suffer from systolic heart failure. 21 subjects (4.1%) died during the follow-up of about 4 years. Median LVEF of decedents was >60%. The plasma concentrations of all biomarkers IGFBP7, but not of mimecan & endostatin were significantly higher in decedents.

The following table provides an univariate Cox analyses for the association between biomarker concentrations and all-cause mortality (HR: Hazard Ratio)

|  | HR | p |
| --- | --- | --- |
| NT-proBNP | 2.271 | <0.0001 |
| hs-cTnT | 4.180 | <0.0001 |
| IGFBP7 | 12.081 | <0.0001 |
| Mimecan | 0.941 | 0.882 |
| Endostatin | 1.161 | 0.839 |

NT-proBNP, hs-cTnT and IGFBP7, but not Mimecan and endostatin are significantly associated with all-cause mortality at univariate analyses. Interestingly, the largest hazard ratios are observed for IGFBP7. Thus, IGFBP7 is a better predictor for the risk of mortality than Troponin T or NT-proBNP.

The following table provides a multivariable Cox analysis for the association between biomarker concentrations and all-cause mortality after adjustment.

|  | HR | p |
| --- | --- | --- |
| NT-proBNP | 2.122 | 0.001 |
| hs-cTnT | 3.040 | 0.004 |
| IGFBP7 | 10.312 | 0.015 |
| Mimecan | 0.829 | 0.614 |
| Endostatin | 0.389 | 0.261 |

After adjustment, NT-proBNP, hs-cTnT and IGFBP7 are significantly associated with all-cause mortality. The largest hazard ratios is observed for IGFBP7.

Detection of Subtle Cardiac Changes

Seven markers (NT-ProBNP, hsTnT, Endostatin, IGFBP7 Mimecan/Osteoglycin, FGF-23, VitaminD) were examined in 550 elderly subjects selected from the PREDICTOR study. The clinical characteristics of this subcohort are described above. Cardiac Troponin, FGF-23, IGBP7, endostatin and mimecan levels are elevated, while Vitamin D is reduced in subjects with subtle myocardial changes, LVH and/or reduced MFS and with preserved ejection fraction (LVEF>55%). Thus, the determination of these markers will help to identify an intermediate phenotype in the progression from hypertension to heart failure. The ratio of FGF-23/Vitamin D may be determined in addition. An increased level of a marker selected preferably from NT-ProBNP, Endostatin, cardiac Troponin, or from FGF-23 (preferably the ratio of FGF-23/vitamin D) and mimecan relative to the respective reference level indicates that the patient suffers from subtle cardiac changes, MFS and/or LVH.

The following table provides sensitivities at 80% specificity of the combination of NT-ProBNP or cardiac Troponin T and Endostatin in the detection of samples of early HF stages (n=352) in the 550 patient subcohort of the Predictor study. Samples derived from patients with borderline LVH or mildly elevated LV masses, (females with LV masses of 96-121 $g/m^2$; males with LV masses of 116-148 $g/m^2$) or abnormal MFS or stage C. The control group comprised samples of patients with HF stages 0 or A (n=211).

|  | Specificity | Sensitivity |
| --- | --- | --- |
| NT-ProBNP | 80% | 113 (32%) |
| cTnT hs | 80% | 141 (40%) |
| Endostatin | 80% | 141 (40%) |
| NT-ProBNP + Endostatin | 80% | 149 (43%) |
| cTnThs + Endostatin | 80% | 166 (47%) |

As can be derived from the table, the combination of NT-ProBNP or cTnThs with endostatin detects a higher rate of patients with subtle cardiac changes, LVH, abnormal MFS, early heart failure stages B and stage C versus both markers alone. As can be derived from the table, several patients with borderline mild to moderate abnormal LV mass (95-132 $g/m^2$ in case of females and 116-149 $g/m^2$ in case of males) are not detected with either NT-ProBNP (239/352) or with cTnT (211/352) or Endostatin (211/352) alone at a specificity of 80% in the control group (211 samples stage 0 or A without subtle myocardial changes).

The combination of two markers resulted in a slightly improved sensitivity of 43% (Endostatin and NT-ProBNP) versus both markers alone 32% (NT-ProBNP) and 40% (Endostatin) at 80% specificity. The combination of two markers resulted in a even more improved sensitivity of 47% (Endostatin and cTnThs) versus both markers alone 40% (cTnThs) and 40% (Endostatin) at 80% specificity. The combination of cTnT and Endostatin is particularly preferred for the detection of early HF stages with mildly elevated LV masses or abnormal MFS.

A further preferred marker combination for detection of subtle myocardial changes, abnormal MFS or mildly elevated LV masses or borderline LVH in samples of patients with early HF stages comprises high sensitive cardiac Troponin, endostatin and the ratio of FGF-23 to vitamin D.

Figure 1B:
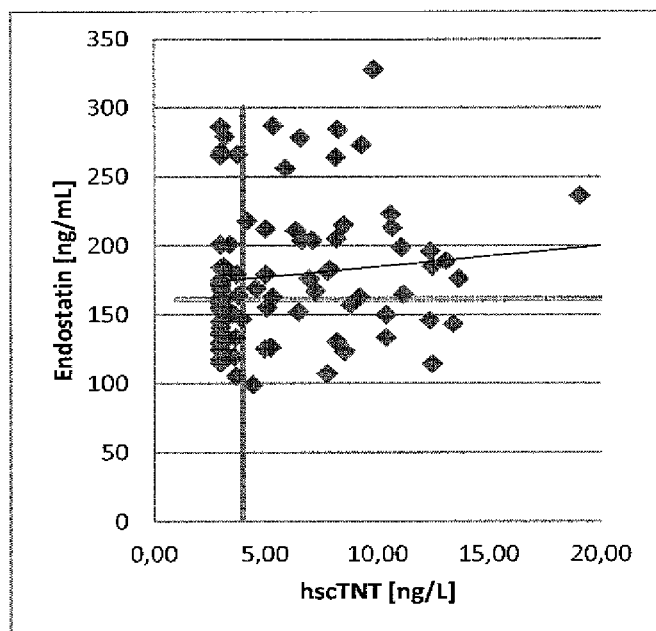
FIG. 1B: Endostatin and cTnT levels in female subjects with borderline LVH/mildly elevated LV masses.
Figure 2A:
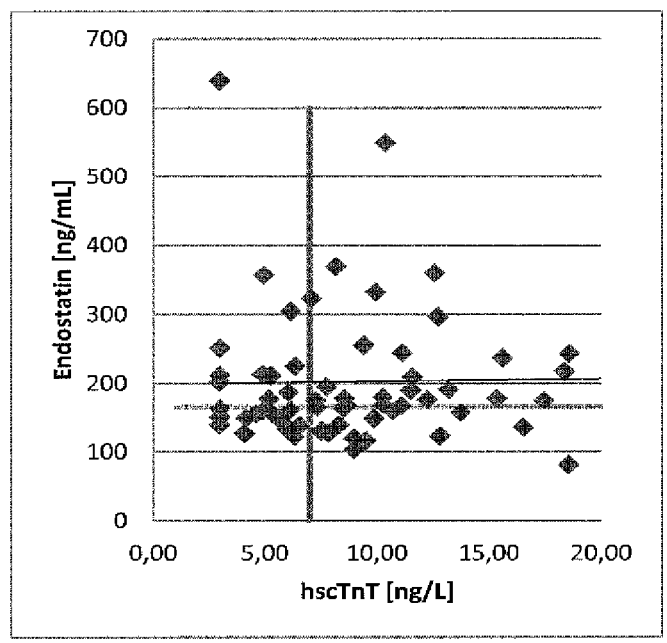
FIG. 2A: Endostatin and cTnT levels in male subjects with borderline LVH/mildly elevated LV masses.
Figure 2B:
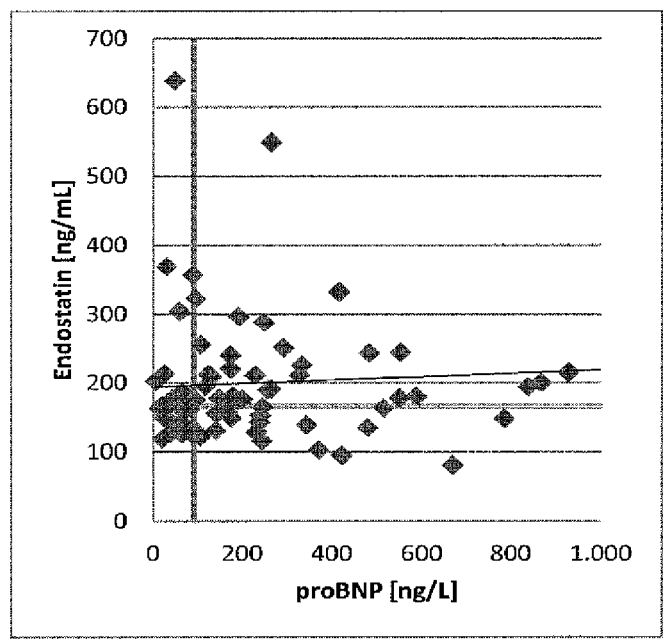
FIG. 2B: Endostatin and NT-ProBNP levels in male subjects with borderline LVH/mildly elevated LV masses.

The marker levels of endostatin, NT-ProBNP and cTnT in females or males with borderline or mildly elevated LV masses are shown in FIGS. 1 and 2

As it can be derived from the figures, several samples of subjects with subtle myocardial changes are associated with low marker levels (below median indicated by line). The Median relates to marker levels in the control group (stage 0 or A without subtle myocardial changes). As it can be derived further from graphs different sample subsets are detected by the different markers. In particular in female subjects a marker combination of endostatin and NT-ProBNP or of endostatin and cTnT is preferred to improve sensitivity.

Case Studies

A 75 year old female patient with class A heart failure has a BMI below 30 kg/m' and hypertension. Troponin T and FGF-23 are determined in a serum sample obtained from the patient (with the kits described above). The Troponin T value is 7.1 pg/ml, the FGF-23 value 93 RU/ml (relative units/ml, Immunotopics) which is indicative that imaging based diagnostic assessment should be carried out. To confirm the biomarker based assessment, imaging based diagnostic testing of diastolic dysfunction is performed using a Doppler-derived multiparametric algorithm including Doppler-derived indexes of transmitral flow and pulmonary vein flow, and tissue Doppler imaging of the lateral mitral annulus (E/e') as an indirect estimate of increased LV filling pressures. The patient is diagnosed to have diastolic dysfunction. This confirms that detection of troponin T and FGF-23 allows for reliable assessment of whether a subject shall be subjected to an imaging based diagnostic assessment.

A 71 year old male patient with class A heart failure has a BMI below 30 kg/m$^2$ and hypertension. Troponin T and FGF-23 are determined in a serum sample obtained from the patient. The Troponin T value is below 3.0 pg/ml, the FGF-23 value is 59 RU/ml which is indicative that imaging based diagnostic assessment is not needed. To confirm the biomarker-based assessment, imaging based diagnostic testing for diastolic dysfunction is performed using a Doppler-derived multiparametric algorithm including Doppler-derived indexes of transmitral flow and pulmonary vein flow, and tissue Doppler imaging of the lateral mitral annulus (E/e') as an indirect estimate of increased LV filling pressures. The patient is diagnosed not to have diastolic dysfunction, thus confirming that detection of troponin T allows for reliable assessment of whether a subject shall be subjected to an imaging based diagnostic assessment.

A 69 year old female patient with class A heart failure has a BMI below 30 kg/m$^2$ and hypertension. Troponin T and FGF-23 determined in a serum sample obtained from the patient. The Troponin T value is 6.5 pg/ml, the FGF-23 value is 99 RU/ml which is indicative that imaging based diagnostic assessment is needed. Therefore imaging based diagnostic testing for systolic function is performed to confirm the biomarker-based assessment. LV systolic function is calculated at the midwall level (midwall fractional shortening, MFS) using a modified ellipsoidal model. In addition, LV mass is calculated according to the recommendations of the American Society of Echocardiography and the European Association of Echocardiography (EAE). The patient is diagnosed to have subnormal MFS and normal LVmass, thus confirming that detection of troponin T allows for reliable assessment of whether a subject shall be subjected to an imaging based diagnostic assessment.

A 76 year old male patient with class A heart failure has a BMI below 30 kg/m2 and hypertension. Troponin T is determined in a serum sample obtained from the patient. The Troponin T value is below 3 pg/ml, the FGF-23 value is 64 RU/ml which is indicative that imaging based diagnostic assessment is not needed. Diagnosis of systolic function is performed to confirm the biomarker-based assessment. LV systolic function is calculated at the midwall level (midwall fractional shortening, MFS) using a modified ellipsoidal model. In addition LV mass is calculated according to the recommendations of the American Society of Echocardiography and the European Association of Echocardiography (EAE). The patient is diagnosed to have normal MFS and normal LVmass which confirms that detection of troponin T allows for reliable assessment of whether a subject shall be subjected to an imaging based diagnostic assessment.

A 66 year old female patient with class A heart failure is has a BMI of 40 kg/m$^2$ and hypertension and diabetes. Troponin T is determined in a serum sample obtained from the patient. The Troponin T value is below 3.0 pg/ml which is indicative that imaging based diagnostic assessment is not needed. The patient is informed to return to a follow up visit in 12 months or if symptoms worsen. After 12 months the patient comes to a follow up visit. Troponin T is determined in a serum sample obtained from the patient. The Troponin T value is 3.5 pg/ml which is indicative that imaging based diagnostic assessment is needed. Therefore imaging based diagnostic testing for systolic function is performed to confirm the troponin based assessment. LV systolic function is calculated at the midwall level (midwall fractional shortening, MFS) using a modified ellipsoidal model. In addition LV mass is calculated according to the recommendations of the American Society of Echocardiography and the European Association of Echocardiography (EAE). The patient is diagnosed to have subnormal MFS and normal LVmass which confirms that detection of troponin T allows for reliable assessment of whether a subject shall be subjected to an imaging based diagnostic assessment Conclusions Conclusions: hs-cTnT and FGF-23 levels are elevated in elderly subjects with subtle alterations of LV geometry and function, and may help to identify an early intermediate phenotype in the progression to heart failure. In particular hs-cTnT levels and the ratio of FGF-23 levels/vitamin D levels are elevated in elderly subjects with normal LV mass index and abnormal MFS.

Widespread application of echocardiographic screening for systolic/diastolic dysfunction has been limited by cost-to-benefit consideration. This disadvantage, however, could be overcome by applying the method of the present invention. By determining the amount of a cardiac Troponin and/or of FGF-23, it is possible the assess whether an imaging based assessment of cardiac function would be required, or not. Accordingly, by carrying out the method of the present invention unnecessary health care expenses can be avoided.

Detection of subtle early myocardial changes and/or early LVH can be improved by combinations of Biomarkers selected from NT-ProBNP, Troponin T and endostatin. In addition the markers mimecan, FGF23/vitamin and GDF15 can be determined in order to detect subtle early myocardial changes.

The detection of a the markers referred to herein will allow for stratifying if a hypertensive patient having a normal left ventricular mass and who does not suffer from left ventricular hypertrophy should be subjected to an imaging based diagnostic assessment for diagnosing a diastolic or systolic dysfunction (preferably echocardiography), wherein an increased level of marker(s) relative to the respective reference level indicates that the patient should be subjected to the imaging based diagnostic assessment and wherein any other level of the marker(s) indicate(s) that the patient should not be subjected to the imaging based diagnostic assessment.

In the present population of elderly people at low risk, elevated levels of FGF-23 and low levels of vitamin D identify individuals with an subtle structural changes and predict all-cause mortality.

The invention claimed is:

1. A method for assessing abnormal midwall fractional shortening in a subject suffering from hypertension wherein the subject does not have left ventricular hypertrophy (LVH), said method comprising the steps of
   a) determining the amount(s) of a cardiac Troponin and/or Fibroblast Growth Factor 23 (FGF-23) in a serum or plasma sample from the subject,
   b) comparing the determined amount in step (a) to a reference amount,
   c) identifying the subject to be subjected to an imaging based diagnostic assessment for diagnosing abnormal midwall fractional shortening when an amount of a cardiac Troponin and/or FGF-23 in the sample as set forth in step a) is larger than the reference amount, and
   d) subjecting the subject identified in step c) to said imaging based assessment for diagnosing abnormal midwall fractional shortening, thereby detecting the presence or absence of abnormal midwall fractional shortening.

2. The method of claim 1 wherein cardiac Troponin is determined in step a).

3. The method of claim 1 wherein FGF-23 is determined in step a).

4. The method of claim 1 wherein both cardiac Troponin and FGF-23 are determined in step a).

5. The method of claim 1 wherein the cardiac Troponin is Troponin T or Troponin I.

6. The method of claim 1, wherein the reference amount is a calculated reference amount.

7. The method of claim 1, wherein
   the reference amount is derived from a subject or group of subjects which is (are) known to be susceptible to an imaging based diagnostic assessment, wherein an amount of the cardiac Troponin and/or FGF-23 which is (are) essentially identical or which is (are) larger than the reference amount(s) identifies (identify) that the subject shall be subjected to an imaging based diagnostic assessment.

8. The method of claim 1, wherein the reference amount is the amount of the cardiac Troponin and/or FGF-23 in a first sample that has been obtained from the subject prior to the sample as set forth in step a) of claim 1.

9. The method of claim 8, wherein the first sample has been obtained 6 to 18 months prior to the sample as set forth in step a) of claim 1.

10. The method of claim 8, wherein an amount of a cardiac Troponin in the sample as set forth in step a) of claim 1 that is at least 10% larger than the amount in the first sample, and/or wherein an amount of FGF-23 in the sample as set forth in step a) of claim 1 is at least 5% larger than the amount in the first sample identifies (identify) that the subject shall be subjected to an imaging based diagnostic assessment.

11. The method of claim 8, wherein the subject did not suffer from abnormal MFS at the time at which the first sample has been obtained.

12. The method of claim 1, wherein the imaging based assessment is echocardiography or magnetic resonance imaging.

13. The method of claim 1, wherein steps a) through c) are performed using a system comprising:
   a) an analyzer unit configured to bring the sample into contact with a detection agent that specifically binds to cardiac Troponin for a time sufficient to allow for the formation of a complex of said detection agent and cardiac Troponin from the sample and/or a detection agent that specifically binds to FGF-23 for a time sufficient to allow for the formation of a complex of said detection agent and FGF-23 from the sample,
   b) an analyzer unit configured to measure the amounts of the formed complexes, wherein said amounts of the formed complexes are proportional to the amounts of the cardiac Troponin and/or FGF-23,
   c) a computing device having a processor and in operable communication with said analyzer units, and
   d) a non-transient machine readable media including a plurality of instructions executable by the processor, wherein the instructions when executed transform the amount of the formed complexes into amount(s) of the cardiac Troponin and/or FGF-23 in the sample and compare said amount(s) to reference(s).

* * * * *